(12) United States Patent
Campadelli et al.

(10) Patent No.: US 9,157,071 B2
(45) Date of Patent: Oct. 13, 2015

(54) HERPES SIMPLEX VIRUS (HSV) WITH MODIFIED TROPISM, USES AND PROCESS OF PREPARATION THEREOF

(75) Inventors: Gabriella Campadelli, Bologna (IT); Laura Menotti, Bologna (IT)

(73) Assignee: ALMA MATER STUDIORUM-UNIVERSITA DI BOLOGNA, Bologna (IT)

( * ) Notice: Subject to any disclaimer, the term of this patent is extended or adjusted under 35 U.S.C. 154(b) by 425 days.

(21) Appl. No.: 12/953,528

(22) Filed: Nov. 24, 2010

(65) Prior Publication Data
US 2011/0318268 A1 Dec. 29, 2011

Related U.S. Application Data

(63) Continuation of application No. PCT/IT2008/000358, filed on May 29, 2008.

(51) Int. Cl.
| | | |
|---|---|---|
| A61K 35/76 | (2015.01) |
| C12N 15/79 | (2006.01) |
| A61K 35/00 | (2006.01) |
| C12N 7/01 | (2006.01) |
| A61K 49/00 | (2006.01) |
| C12N 7/00 | (2006.01) |
| C07K 14/005 | (2006.01) |
| A61K 35/763 | (2015.01) |

(52) U.S. Cl.
CPC ............... *C12N 7/00* (2013.01); *A61K 35/763* (2013.01); *C07K 14/005* (2013.01); *C07K 2317/622* (2013.01); *C07K 2319/33* (2013.01); *C07K 2319/61* (2013.01); *C07K 2319/74* (2013.01); *C12N 2710/16622* (2013.01); *C12N 2710/16632* (2013.01); *C12N 2710/16722* (2013.01); *C12N 2810/85* (2013.01)

(58) Field of Classification Search
CPC . A61K 35/763; A61K 38/1774; C12N 15/86; C12N 2710/16632; C12N 2710/16634; C12N 15/63; C12N 2710/16643; C12N 2710/16671; C12N 15/869; C12N 2710/16611; C07K 14/005; C07K 16/00; C07K 16/087
See application file for complete search history.

(56) References Cited

U.S. PATENT DOCUMENTS

| | | | |
|---|---|---|---|
| 6,716,422 B1 | 4/2004 | Gajewski et al. | |
| 7,943,144 B2 * | 5/2011 | Brown et al. | 424/199.1 |
| 2002/0090709 A1 | 7/2002 | Begent et al. | |
| 2003/0007974 A1 | 1/2003 | Nanus et al. | |
| 2003/0171551 A1 | 9/2003 | Rosenblatt et al. | |
| 2004/0115688 A1 | 6/2004 | Cheung et al. | |
| 2004/0116379 A1 | 6/2004 | Cheung | |
| 2004/0180386 A1 | 9/2004 | Carr et al. | |
| 2005/0271620 A1 * | 12/2005 | Brown et al. | 424/93.2 |
| 2007/0093443 A1 | 4/2007 | Madison et al. | |
| 2007/0243170 A1 * | 10/2007 | Roizman et al. | 424/93.6 |
| 2008/0003202 A1 | 1/2008 | Guyon et al. | |
| 2010/0272691 A1 * | 10/2010 | Conner | 424/93.6 |
| 2011/0244576 A1 * | 10/2011 | Brown et al. | 435/475 |

FOREIGN PATENT DOCUMENTS

| | | |
|---|---|---|
| WO | 2004033639 A | 4/2004 |
| WO | 2006048777 A2 | 5/2006 |
| WO | 2007149406 A2 | 12/2007 |

OTHER PUBLICATIONS

Menotti L, Cerretani A, Hengel H, Campadelli-Fiume G. Construction of a fully retargeted herpes simplex virus 1 recombinant capable of entering cells solely via human epidermal growth factor receptor 2. J Virol. Oct. 2008;82(20):10153-61. Epub Aug. 6, 2008.*
Campadelli-Fiume G, Amasio M, Avitabile E, Cerretani A, Forghieri C, Gianni T, Menotti L. The multipartite system that mediates entry of herpes simplex virus into the cell. Rev Med Virol. Sep.-Oct. 2007;17(5):313-26.*
Menotti L, Cerretani A, Campadelli-Fiume G. A herpes simplex virus recombinant that exhibits a single-chain antibody to HER2/neu enters cells through the mammary tumor receptor, independently of the gD receptors. J Virol. Jun. 2006;80(11):5531-9.*
Lorimer IA, Lavictoire SJ. Targeting retrovirus to cancer cells expressing a mutant EGF receptor by insertion of a single chain antibody variable domain in the envelope glycoprotein receptor binding lobe. J Immunol Methods. Apr. 3, 2000;237(1-2):147-57.*
Conner J, Braidwood L, Brown SM. A strategy for systemic delivery of the oncolytic herpes virus HSV1716: redirected tropism by antibody-binding sites incorporated on the virion surface as a glycoprotein D fusion protein. Gene Ther. Dec. 2008;15(24):1579-92. Epub Aug. 14, 2008.*
Nakano K, Asano R, Tsumoto K, Kwon H, Goins WF, Kumagai I, Cohen JB, Glorioso JC. Herpes simplex virus targeting to the EGF receptor by a gD-specific soluble bridging molecule. Mol Ther. Apr. 2005;11(4):617-26.*
Dean,H.J., Terhune,S.S., Johnson,R.M. and Spear,P.G. Glycoprotein D precursor. GenBank Acc. No. Q05059. Dep. Apr. 1, 2004.*
Ward,M., Lin,C., Victoria,D.C., Fox,B.P., Fox,J.A., Wong,D.L., Meerman,H.J., Pucci,J.P., Fong,R.B., Heng,M.H., Tsurushita,N., Gieswein,C., Park,M. and Wang,H. humanized antibody light chain variable region, partial [synthetic construct]. GenBank Acc. No. AAS07025. Dep. May 6, 2004.*
Ward,M., Lin,C., Victoria,D.C., Fox,B.P., Fox,J.A., Wong,D.L., Meerman,H.J., Pucci,J.P., Fong,R.B., Heng,M.H., Tsurushita,N., Gieswein,C., Park,M. and Wang,H. humanized antibody light chain variable region, partial [synthetic construct]. GenBank Acc. No. AAS07024. Dep. May 6, 2004.*
Cerretani A. Molecular Basis of Herpes Simplex Virus Entry Into the Cell and Retargeting of the Viral Tropism for the Design of Oncolytic Herpesviruses. Dottorato di Ricerca in Biologia Funzionale dei Sistemi Cellulari e Molecolari. Mar. 10, 2008. http://amsdottorato.unibo.it/685/1/Tesi_Cerretani_Arianna.pdf.*

(Continued)

*Primary Examiner* — Benjamin P Blumel
*Assistant Examiner* — Rachel Gill
(74) *Attorney, Agent, or Firm* — Lucas & Mercanti LLP

(57) ABSTRACT

A modified Herpes Simplex Virus (HSV), which has a portion of gD (glycoprotein D) of the glycoproteic envelope deleted and a heterologous single chain antibody inserted in place of such deleted portion; the modified HSV is capable of infecting cells through receptor HER2/ErbB2 but not through receptors HVEM/HveA and nectin1/HveC; uses of the modified HSV and a process of the preparation thereof are also disclosed.

17 Claims, 15 Drawing Sheets

(56) References Cited

OTHER PUBLICATIONS

Tanaka, M., et al., "Construction of an Excisable Bacterial Artificial Chromsome Containing a Full-Length Infectious Clone of Herpes Simplex Virus Type 1: Viruses Reconstituted from the Clone Exhibit Wild-Type Properties in Vitro and in Vivo," Journal of Virology 77(2): 1382-1391 (Jan. 2003).

Tur, M.K., et al., "An Anti-GD2 Single Chaine Fv Selected by Phage Display and Fused to Pseudomonas Exotoxin A Develops Specific Cytotoxic Activity Against Neuroblastoma Derived Cell Lines," International Journal of Molecular Medicine 8: 579-584 (2001).

De Vries, E., et al., "Positron Emission Tomography: Measurement of Transgene Expression," Methods 27:234-241 (2002).

De Vries, E., et al., "Scintigraphis Imaging of HSVtk Gene Therapy," Current Pharmaceutical Design 8: 1435-1450 (2002).

Wong, J., et al., "Pilot Trial Evaluating an 123I-Labeled 80-Kilodalton Engineered Anticarcinoembryonic Antigen Antibody Fragment (cT84.66 Minibody) in Patients with Colorectal Cancer," Clin. Cancer Res 10: 5014-5021 (Aug. 2004).

Yamamoto, T., et al., "Similarity of Protein Encoded by the Human c-erb-B-2 Gene to Epidermal Growth Factor Receptor," Nature 319: 230-234 (1986).

Zhou, G., et al., "Engineered Herpes Simplex Virus 1 is Dependent on IL13Ralpha2 Receptor for Cell Entry and Independent of Glycoprotein D Receptor Interaction," Proc Natl Acad Sci USA 99(23):15124-15129 (2002).

Zhou, G., et al., "Construction and Properties of a Herpes Simplex Virus 1 Designed to Enter Cells Soley Via the IL-13 x2 Receptor." PNAS 103(14):5508-5513 (Apr. 2006).

Zhou, G., et al., "Glycoprotein D or J Delivered in trans Blocks Apoptosis in SK-N-SH Cells Induced by a Herpes Simplex Virus 1 Mutant Lacking Intact Genes Expressing Both Glycoproteins," Journal of Virology 74(24): 11782-11791 (Dec. 2000).

Menotti, L., et al., "A Herpes Simplex Virus Recombinant that Exhibits a Single-Chain Antibody to HER2/neu Enters Cells Through the Mammary Tumor Receptor, Indepedently of the gD Receptors," Journal of Virology, 80(11): pp. 5531-5539, Jun. 2006.

Zhou, G., et al., "The Domains of Glycoprotein D Required to Block Apoptosis Induced by Herpes Simplex Virus 1 are Largely Distinct from those Involved in Cell-Cell Fusion and Binding to Nectin1," Journal of Virology, 77(6): pp. 3759-3767, Mar. 2003.

Krummenacher, C., et al. "Structure of Unliganded HSV gD Reveals a Mechanism for Receptor-Mediated Activation of Virus Entry," EMBO (European Molecular Biology Organization Journal), 24(23): pp. 4144-4153 (Dec. 2005).

Jogger, C.R., et al., "Effects of Linker-Insertion Mutations in Herpres Simplex Virus 1 gD on Glycoprotein-Induced Fusion with Cells Expressing HVEM or Nectin-1," Virology 318(1): pp. 318-326 (Jan. 5, 2004).

Connolly, S., et al., "Potential Nectin-1 Binding Site on Herpes Simplex Virus Glycoprotein D," Journal of Virology 79(2): pp. 1282-1295 (Jan. 2005).

Zhou, G., et al., "Engineered Herpes Simplex Virus 1 is Dependent on IL13Ralpha2 Receptor for Cell Entry and Independent of Glycoprotein D Receptor Interaction," Proceedings of the National Academy of Sciences of USA, National Academy of Science, 99(23): pp. 15124-15129 (Nov. 12, 2002).

Lucignani, et al., "Molecular Imaging of Cell-Mediated Cancer Immunotherapy," Trends in Biotechnology 24(9): pp. 410-418 (Sep. 1, 2006).

Menotti, L., et al., "Construction of a Fully Retargeted Herpes Simplex Virus 1 Recombinant Capable of Entering Cells Solely Via Human Epidermal Growth Factor Receptor 2," Journal of Virology 82(20): pp. 10153-10161 (Oct. 2008).

Zhou, G., et al., "Construction and Properties of a Herpes Simplex Virus 1 Designed to Enter Cells Solely Via the IL-13alpha2 Receptor," Proceedings of the National Academy of Sciences of USA, National Academy of Science, 103 (14): pp. 5508-5513 (Apr. 4, 2006).

Adler, H., et al., "Cloning and Mutagenesis of the Murine Gammaherpesvirus 68 Genome as an Infectious Bacterial Artifical Chromosome," J. Virology 74(15): pp. 6964-6974 (2000).

Altschul, et al., Gapped BLAST and PSI-BLAST: A New Generation of Protein Database Search Programs, Nucleic Acids Res. 25(17): pp. 3389-3402.

Boldicke, T., et al., "Anti-VEGFR-2 scFvs for Cell Isolation. Single-Chain Antibodies Recognizing the Human Vascular Endothelial Growth Factor Receptor-2 (VEGFR-2/flk-1) on the Surface of Primary Endothelial Cells and Preselected CD34+ Cells from Cord Blood," Stem Cells 19: pp. 24-36 (2001).

Borst, E.M., et al., "Cloning of the Human Cytomegalovirus (HCMV) Genome as an Infectious Bacterial Artifical Chromosome in *Escherichia coli*: A New Approach for Construction of HCMV Mutants," J. Virol 73(10): pp. 8320-8329 (1999).

Bowie, et al., "Deciphering the Message in Protein Sequences: Tolerance to Amino Acid Substitutions," Science 247: pp. 1306-1310(1990).

Brunettti, C.R., et al., "Role of Mannose-6 Phosphate Receptors in Herpes Simplex Virus Entry Into Cells and Cell-to-Cell Transmission," J. Virol69(6): pp. 3517-3528 (1995).

Campadelli-Fiume, et al., "The Novel Receptors that Mediate the Entry Herpes Simplex Viruses and Animal Alphaperpesviruses into Cells," Reviews in Medical Virology, 10: pp. 305-319 (2000).

Campadelli-Fiume, et al., The Multipartite System that Mediates the Entry of Herpes Simplex Viruses Into the Cell, Rev. Med. Viol., 17: pp. 313-326 (2007).

Carmeliet, P., "VEGF as a Key Mediator of Angiogenesis in Cancer," Oncology 69: pp. 4-10 (2005).

Carpenter, G., "Receptor Tyrosine Kinase Substrates: SRC Homology Domains and Signal Transduction," FASEB Journal, 6: pp. 3283-3289 (1992).

Cherepanov, P.P., et al., "Gene Disruption in *Escherichia coli*: TcR and KmR Cassettes with the Option of Flp-Catalyzed Excision of the Antibiotic-Resistance Determinant," Gene, 158: pp. 9-14 (1995).

Chowdhury, et al., "Efficient Retroviral Vector Targeting of Carcinoembryonic Antigen-Positive Tumors," Mol. Ther. 9(1): pp. 85-92 (2004).

Cocchi, F., et al., "The Ectodomain of a Novel Member of the Immunoglobulin Subfamily Related to the Poliovirus Receptor has the Attributes of a Bona Fide Receptor for Herpes Simplex Viruses Types 1 and 2 in Human Cells," J. Virol., 72(12): pp. 9992-10002.

Datsenko, K.A., et al., One-Step Inactivation of Chromosomal Genes in *Escherichia coli* K-12 Using PCR Products, Proc. Natl. Acad. Sci. 97(12): pp. 6640-6645 (2000).

Degiovanni, C., et al., "Immunoprevention of HER-2/neu Transgenic Mammary Carcinoma Through an Interleukin 12-Engineered Allogeneic Cell Vaccine," Cancer Res. 64: pp. 4001-4009 (2004).

Devereux, et al., "A Comprehensive Set of Sequence Analysis Programs for the VAX," Nucleic Acids Research, 12 (1): pp. 387-395 (1984).

Ejercito, P.M., et al., "Characterization of Herpes Simplex Virus Strains Differing in Their Effects on Social Behavior of Infected Cells," J. Gen. Virol., 2: pp. 357-364 (1968).

Holbro, T., et al., "ErbB Receptors: Directing Key Signaling Networks Throughout Life," Annu. Rev. Pharmacol. Toxicology, 44: pp. 195-217 (2004).

Horak, E. et al., "Isolation of scFvs to In Vitro Produced Extracellular Domains of EGFR Family Members," Cancer Biother Radiopharm, 20(6): pp. 603-613 (2005).

Hu, S., et al., "Minibody: A Novel Engineered Anti-Carcinoembryonic Antigen Antibody Fragment (single-chain Fv-C H3) Which Exhibits Rapid, High-Level Targeting of Xenografts," Cancer Research, 56: pp. 3055-3061 (1996).

Hynes, N.E., et al., "ERBB Receptors and Cancer: The Complexity of Targeted Inhibitors," Nat. Rev Cancer, 5: 341 (2005).

Hynes, N.E., et al., "The Biology of erbB-2/neu/HER-2 and Its Role in Cancer," Biochim. Biophys. Acta, 1198: pp. 165-184 (1994).

Karlin, S., et al., Applications and Statistics for Multiple High-Scoring Segments in Molecular Sequences, Proc. Natl. Acad. Sci., 90: pp. 5873-5877 (1993).

(56) References Cited

OTHER PUBLICATIONS

Karlin, S., et al., "Methods for Assessing the Statistical Significance and Molecular Sequence Features by Using General Scoring Schemes," Proc. Natl. Acad. Sci., 87: pp. 2264-2268 (1990).

Kenanova, et al., "Tailoring the Pharmacokinetics and Positron Emission Tomography Imaging Properties of Anti-Carcinoembryonic Antigen Single-Chain Fv-Fc Antibody Fragments," Cancer Res., 65(2): pp. 622-631 (2005).

Kushner, B.H., et al., "Phase II Trial of the Anti-GD2 Monoclonal Antibody 3F8 and Granulocyte-Macrophage Colony-Stimulating Factor for Neuroblastoma," Journal of Clinical Oncology, 19(22): pp. 4189-4194 (2001).

Laquerre, S., et al., "Heparan Sulfate Proteoglycan Binding by Herpes Simplex Virus Type 1 Glycoproteins B and D, Which Differ in Their Contributions to Virus Attachment, Penetration, and Cell-to-Cell Spread," J. Virol., 72(7): pp. 6119-6130 (1998).

Mayer, A. et al., "Radioimmunoguided Surgery in Colorectal Cancer Using a Genetically Engineered Anti-CEA Single-Chain Fv Antibody," Clin. Cancer Res. 6: pp. 1711-1719 (2000).

Messerle, M., et al., "Cloning and Mutagenesis of a Herpesvirus Genome as an Infectious Bacterial Artificial Chromosome," Proc. Natl. Acad. Sci 94: pp. 14759-14763 (1997).

Muyrers, J.P., et al., "Rapid Modification of Bacterial Artificial Chromosomes by ET-Recombination," Nucleic Acids Res. 27(6): pp. 1555-1557 (1999).

Nakamura, T., et al., "Antibody-Targeted Cell Fusion," Nat. Biotechnology 22(3): pp. 331-336 (2004).

O'Connor, M., et al., "Construction of Large DNA Segments in *Escherichia coli*," Science pp. 1307-1132 (1989).

Olafsen, T., et al., "Covalent Disulfide-Linked Anti-CEA Diabody Allows Site-Specific Conjugation and Radiolabeling for Tumor Targeting Applications," Protein Eng. Des. Sel. 17(1): pp. 21-27 (2004).

Post, L.E., et al., "A Generalized Technique for Deletion of Specific Genes in Large Genomes: Alpha Gene 22 of Herpes Simplex Virus 1 is not Essential for Growth," Cell 25: pp. 227-232 (1981).

Press, M.F., "Expression of the HER-2/neu Proto-Oncogene in Normal Human Adult and Fetal Tissues," Oncogene 5: pp. 953-962 (1990).

Ricci, C., et al., "Expression of HER/erbB Family of Receptor Tyrosine Kinases and Induction of Differentiation by Glial Growth Factor 2 in Human Rhabdomyosarcoma Cells," Int. J. Cancer 87: pp. 29-36 (2000).

Sharma, V., et al., "Molecular Imaging of Gene Expression and Protein Function In Vivo with PET and SPECT," J. Mag. Reson. Imaging 16: 336-351 (2002).

Sidhu, S.S., et al., "Phage-Displayed Antibody Libraries of Synthetic Heavy Chain Complementarity Determining Regions," J. Mol. Biol. 338: pp. 299-310 (2004).

Sodora, D.L., et al., "Influence of Asparagines Linked Oligosaccharides on Antigenicity, Processing and Cell Surface Expression of Herpes Simplex Virus Type 1 Glycoprotein D," J. Virol., 63(12): pp. 5184-5193 (1989).

Soling, A., et al., "Intercellular Localization of Herpes Simplex Virus of the Type 1 Thymidine Kinase Fused to Different Fluorescent Proteins Depends on Choice of Fluorescent Tag," FESB Letter., 527: pp. 153-158 (2002).

Spear, P.G., et al., "Three Classes of Cell Surface Receptors for Alphaherpesvirus Entry," Virology, 275: pp. 1-8 (2000).

\* cited by examiner

HERPES SIMPLEX VIRUS (HSV) WITH MODIFIED TROPISM, USES AND PROCESS OF PREPARATION THEREOF

RELATED APPLICATION

This application is a continuation of International Application No. PCT/IT2008/000358, which designated the United States and was filed on May 29, 2008, published in English. The entire teachings of the above application are incorporated herein by reference.

FIELD OF INVENTION

The present invention relates to a modified herpes simplex virus (HSV), uses of the modified HSV, a pharmaceutical preparation and a process of preparing a modified HSV.

BACKGROUND

A novel frontier in the treatment of tumors is oncolytic virotherapy, whereby a replication competent virus infects the tumor cells, spreads from cell to cell of the tumor and destroys them. Two such tumors are mammary and ovary cancers, that afflict animals such as humans. About 30% of human mammary tumors, as well as some ovary tumors, are highly malignant and metastatic.

These tumors owe their high malignancy and metastaticity to the expression of a specific cell surface molecule receptor, named HER2, that belongs to the family of epidermal growth factor receptors, and are generally treated with surgery or combined surgery and radiotherapy or chemotherapy.

HSV is a pathogen virus for mammalian cells [HSV-1 is e.g. described in Ejercito, P. M., et al. (1968). J Gen Virol 2:357 and its genome has accession number NC-001806 (GenBank)].

HSV enters cells by a multistep process. The first step is attachment to the cell surface, mediated by interaction the glycoproteins gB and gC (Laquerre S., Argnani R., Anderson D. B., Zucchini S., Manservigi R., Glorioso J. C. (1998), J. Virol. 72(7):6119-30). This is followed by the more specific interaction of the virion envelope glycoprotein D (gD) with one of its entry receptors: nectin1/HveC, HVEM/HveA, and O-linked sulphated moieties of heparan sulphate (Spear P. G., Eisenberg R. J., Cohen G. H., (2000) Virology 275:1-9) (Campadelli-Fiume G., Cocchi F., Menotti L., Lopez M. (2000) Reviews in Medical Virology, 10:305-319) (Campadelli-Fiume G. et al. (2007) Rev. Med. Virol., 17:313-326) (the GenBank codes for the receptors are the followings: nectin1 alpha AF060231, nectin1 beta AF110314, HVEM U70321).

In recent years, there have been attempts to use genetically engineered HSVs as oncolytic agents mainly to treat malignant glioma. Inasmuch as wild-type viruses are virulent, target and destroy many different cells and tissues, the candidate oncolytic HSVs have been highly attenuated. The viruses that have reached clinical trials were made dependent for their replication upon the dividing tumor cell by the deletion of two HSV genes, namely the gamma1 43.5 gene—which encodes the ICP34.5 protein whose role is to preclude the shut off of protein synthesis in infected cells, and the UL39 gene—which encodes the large subunit of ribonucleotide reductase. These viruses are marred by low ability to replicate, even in dividing cells, a feature that results in two negative effects. First, administration of such viruses to tumors fails to produce high yield of progeny viruses, capable of spreading from cell to cell of the tumor itself, and thus to amplify the response to any given therapeutic dose of the virus. Second, the viruses are difficult to grow and can hardly be produced in large scale ($10^8$-$10^9$ plaques forming units PFU/ml) to yield the amount of virus required for clinical applications. Furthermore, the preserved ability of the virus to bind to any cell bearing one the natural receptors for the HSV subtracts the virus to the tumor tissues that most need it and diminishes the therapeutic effect of tumor cell killing, and may exert undesired infection of non cancer tissues and cells, including their death by apoptosis. We note that, even if these viruses were retargeted to tumor-specific receptors—they are nonetheless highly attenuated.

Recently HSV retargeted to specific receptors have been genetically engineered so that they can infect cells that need to be destroyed while maintaining high capacity to replicate and spread from cell to cell. Though such viruses have a good ability to spread among tumor cells, they still undesirably infect non cancer tissues and cells.

Patent application having publication number WO2004/033639, whose content is herein fully included, discloses a recombinant HSV, which expresses on its glycoproteic envelope a natural cytokine. Though the use of recombinant HSV of this type has been proposed for treating tumors, it is important to stress that: the targeted receptor has natural ligand of a small size such that it can be readily inserted in gD, and the proposed recombinant HSV is still capable of interacting with receptors nectin1/HveC and HVEM/HveA. In particular, WO2004/033639 fails to identify mutations that would result in a recombinant HSV which is not anymore capable of binding nectin1/HveC and is capable of binding receptors (such as HER2/ErbB2) of diseased cells.

It follows that a need in the art still exists for viral therapeutic agents targeting selectively cells that need to be destroyed. In particular a need exists for viral therapeutic agents targeting receptors that have no natural ligand, and are overexpressed or selectively expressed in diseased cells, such as cancer cells.

SUMMARY

It is an object of the present invention to provide a modified HSV designed to at least partly eliminate the drawbacks of the known art, and which, at the same time, are easy to implement.

Further objects of the present invention are to provide uses of the mentioned modified HSV, pharmaceutical preparations, and a process of preparing the modified HSV.

All references (e.g. patents, patent applications, publications, GenBank sequences, and other published materials) referred to throughout the entire present text, unless noted otherwise, are herein entirely incorporated for completeness of disclosure (incorporated by reference).

Unless the contrary is explicitly specified, the following terms have the hereinafter indicated meaning.

As used herein, "single chain antibody" (scFv) refers to "properly called" single chain antibody (i.e. having two domains connected by a linker) or other similar antibody derivatives (e.g. Single V-Type domains). Advantageously, the "single chain antibodies" are "properly called" single chain antibodies. A non-limiting example of a "properly called" single chain antibody is scHER2 (disclosed in the below reported examples).

As used herein, "percentage of identity" or "% identity" between two aminoacid or nucleotide sequences refers to the percentage of aminoacid or nucleotide residues identical in corresponding positions in the two sequences aligned optimally.

For establishing the "percentage of identity" of the two aminoacid or nucleotide sequences the sequences are aligned; for having an optimal alignment, gaps (deletions or insertions—which may possibly be located at the extremes of the sequences) are possible. The aminoacid or nucleotide residues are compared. Where a position in the first sequence is occupied by the same aminoacid or nucleotide residue which occupies the corresponding position in the second sequence, the molecules are identical in that position. The "percentage of identity" between two sequences is a function of the number of shared identical positions of the sequences [i.e. % identity=(number of identical positions/number of total positions×100].

In accordance to advantageous embodiments, the sequences have the same length (same number of aminoacid residues or nucleotides).

Advantageously, the compared sequences do not have gaps.

The percentage of identity may be obtained using mathematical algorithms. A non limiting example of a mathematical algorithm, which is used to compare two sequences is the algorithm of Karlin and Altschul [Proc. Natl. Acad. Sci. USA 87 (1990) 2264-2268] modified by Karlin and Altschul [Proc. Natl. Acad. Sci. USA 90 (1993) 5873-5877].

In order to obtain alignments also in presence of one or more gaps, it is possible to use methods that give a relatively high penalty for each gap and a lower penalty for each further aminoacid or nucleotide residue (such a further aminoacid or nucleotide residue is defined as an extension of the gap). High penalties result, obviously, in optimal alignments with a lower number of gaps.

An example of a program (software) designed to make such a type of alignment is the BLAST program as disclosed in Altschul, et al., Nucleic Acids Res. 25 (1997) 3389-3402. For this purpose BLASTn and BLASTp programs may be used with default parameters. In the BLAST programs matrix BLOSUM62 is usually used.

An advantageous and non-limiting example of a program for obtaining an optimal alignment is GCG Winsconsin Best-fit package (University of Winsconsin, USA; Devereux et al., 1984, Nucleic Acids Research 12:387). Also in this case, the default parameters (which provide a penalty of −12 for each gap and a penalty of −4 for each extension) are used.

As used herein, "percentage of homology" or "% homology" between two aminoacid or nucleotide sequences refers to the percentage of aminoacid or nucleotide residues homologous in corresponding positions in the two optimally aligned sequences.

The "percentage of homology" between two sequences is established in a manner substantially identical to what has been above described with reference to the determination of the "percentage of identity" except for the fact that in the calculation also homologous positions and not only identical positions are considered.

As far as nucleotide sequences are concerned, two homologous positions may have two different nucleotides, but such two nucleotides, within the respective codon, codify the same aminoacid.

As far as aminoacid sequences are concerned, two homologous positions have two identical or homologous aminoacid. Homologous aminoacid residues have similar chemical-physical properties, for example, aminoacids belonging to a same group: aromatic (Phe, Trp, Tyr), acid (Glu, Asp), polar (Gln, Asn), basic (Lys, Arg, His), aliphatic (Ala, Leu, Ile, Val), with a hydroxyl group (Ser, Thr), with a short lateral chain (Gly, Ala, Ser, Thr, Met). It is expected that substitutions between such homologous aminoacids do not change a protein phenotype (aminoacid conservative substitutions).

Specific examples of conservative substitutions in this technical field are disclosed in several references [e.g. Bowie et al., Science, 247:1306-1310 (1990)].

Further examples of programs and/or articles relating to the establishment of optimal alignments and/or percentages of homology and/or identity are cited, for example, in US2008003202, US2007093443, WO2006048777, WO2007149406.

As used herein, "corresponding position" refers to a position of a aminoacid or nucleotide sequence corresponding (facing), after an alignment has been performed, to a given position of a reference sequence.

For example, a position corresponding to a given position of gD having SEQ ID NO:1 may be identified aligning SEQ ID NO:1 with a peptide sequence of interest; the alignment may be obtained either manually or as above disclosed with reference to the determination of the percentage of identity.

As used herein, "a naked polypeptide chain" refers to a polypeptide that is not post-translationally modified or otherwise chemically modified, but contains only covalently linked aminoacids.

As used herein, "ligand capable of binding in specific conditions a receptor" refers to a ligand which, when inserted in HSV by means of molecular biology techniques, permits the HSV to penetrate in a cell via the interaction with that receptor, which the ligand is designed to bind. In particular, the ligand is capable of binding in specific conditions a receptor, when the HSV, which contains it, is capable of interacting with that receptor passing the tests disclosed in below reported example 5 or analogous tests (with different receptors).

As used herein, "capability of HSV (in particular the modified HSV) of interacting with a receptor" refers to the capability of the HSV of penetrating in a cell via the interaction with that receptor. In particular, also in this case, this capability is evaluated by means of the tests disclosed in below reported example 5 or analogous tests (for different receptors).

BRIEF DESCRIPTION OF THE FIGURES

Non-limiting embodiments of the present invention will be described by way of example with reference to the accompanying drawings, in which.

DESCRIPTION OF ILLUSTRATIVE EMBODIMENTS

Figure 1:
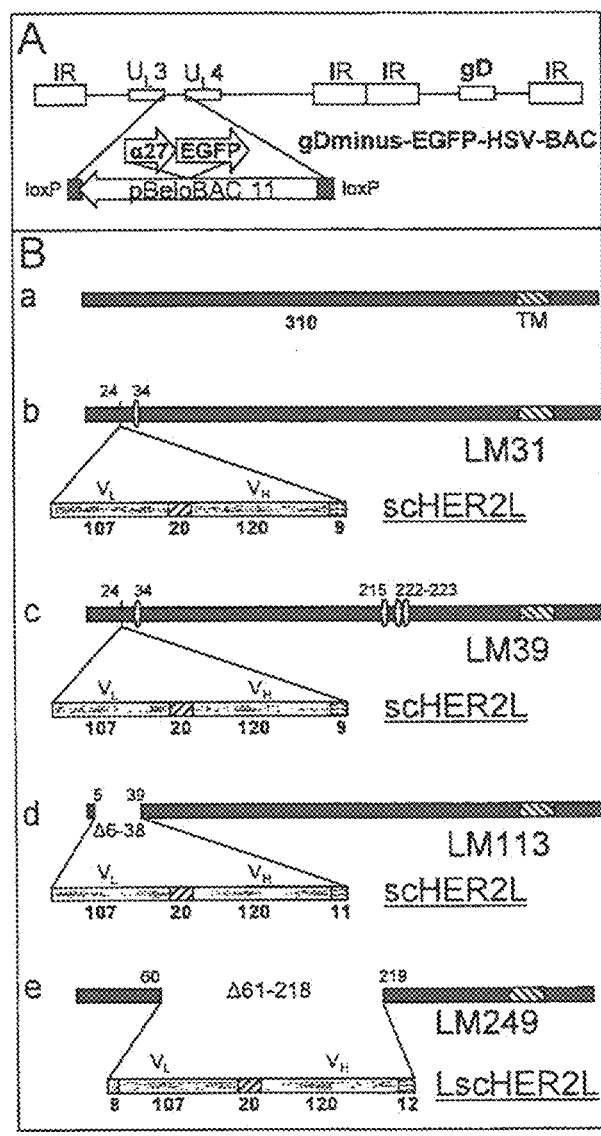
FIG. 1A shows schematic representation of the recombinant HSV-BAC genomes described in this invention. The backbone of gDminus-EGFP-HSV-BAC is shown as example. The backbone of gDminus-EGFP-HSV-BAC is shown. The HSV-BACs derive from pYEbac102 Tanaka, M., H. Kagawa, Y. Yamanashi, T. Sata, and Y. Kawaguchi. 2003. Construction of an excisable bacterial artificial chromosome containing a full-length infectious clone of herpes simplex virus type 1: viruses reconstituted from the clone exhibit wild-type properties in vitro and in vivo. J Virol 77:1382-91. (Tanaka, 2003 #672), that carries pBeloBACll sequences inserted between UL3 and UL4. In gDminus-EGFP-HSV-BAC the reporter cassette (a27-EGFP) is inserted in the BAC sequences. gDminus-LacZ-HSV-BAC has the same structure, but carries LacZ in place of EGFP.
FIG. 1B shows a schematic representations of linear maps of wt-gD (a) and the gD chimeric proteins: (b) gD of recombinant R-LM31, carrying substitution at amino acid residue 34; (c) gD of recombinant R-LM39, carrying mutations at amino acid residues 34, 215, 222 and 223; (d) gD of recombinant R-LM113, carrying scHER2L in place of amino acid residues 6-38; (e) gD of recombinant R-LM249, carrying LscHER2L in place of amino acid residues 61-218. Bold numbers indicate the length in amino acid residues of each fragment. Plain numbers refer to amino acid residues according to wt-gD coordinates. L, linkers. TM, transmembrane domain of gD. $V_H$ and $V_L$, heavy- and light-chain variable domains of the anti-HER2/neu antibody 4D5. Δ, deletion. Bars are drawn to scale.
Figure 2:
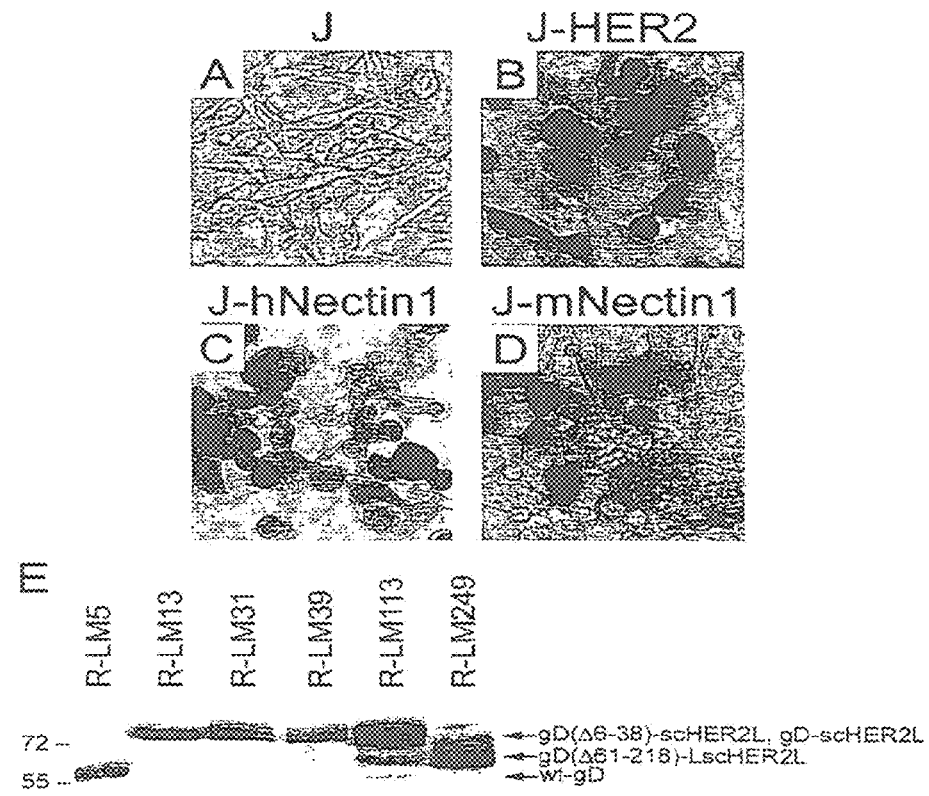
FIG. 2 shows that the recombinant virus R-LM31 is not detargeted from nectin1 receptor. Micrographs of receptor negative J cells (A), and J-HER2 (B), J-hNectin1 (C) and J-mNectin1 (D) expressing human HER2, and human or murine nectin1, respectively, were exposed to R-LM31 at 10 PFU/cell. Infection was monitored as β-galactosidase activity by in situ X-gal staining 16 h following infection. E. Electrophoretic mobility of wt and chimeric gDs expressed in SKOV3 cells infected with R-LM5, R-LM13, R-LM31, R-LM39, R-LM113 and R-LM249 recombinant viruses. Infected cell lysates were separated by SDS-PAGE, transferred to nitrocellulose membranes, and visualized by enhanced chemioluminescence. Numbers to the left represent migration positions of molecular mass markers (in kilodaltons). Arrows indicate the apparent electrophoretic mobility of the wt or chimeric gDs. From bottom to top, wild-type gD (wt-gD) expressed by R-LM5 recombinant virus, gD(Δ61-218)-LscHER2L expressed by R-LM249 recombinant virus, gD(Δ6-38)-scHER2L expressed by R-LM113 recombinant virus. The migration of gD-scHER2L expressed by R-LM13, R-LM31 and R-LM39 is indistinguishable from that of gD(Δ6-38)-scHER2L.
Figure 3:
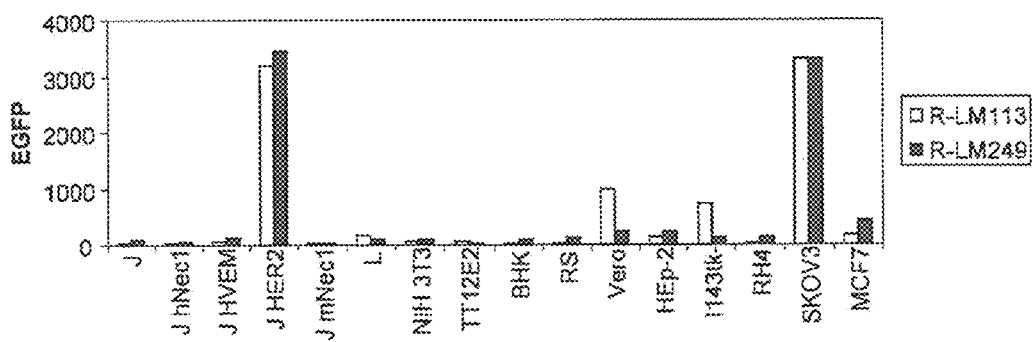
FIG. 3 shows infection of an array of cell lines with R-LM113 and R-LM249 recombinant viruses. Monolayers of the indicated cell lines were infected at 5 PFU/cell, and EGFP reporter gene expression was measured 24 later by means of a fluorometer. Numbers to the left indicate EGFP intensity in arbitrary units.

According to a first aspect of the present invention there is provided a modified herpes simplex virus (HSV) comprising a glycoproteic envelope, which has an heterologous peptide ligand capable of binding in specific conditions a given receptor expressed by diseased cells and substantially not (or little) expressed by non-diseased cells. The glycoproteic envelope being so modified that the capability of the modified HSV of binding in specific conditions receptor nectin1/HveC is reduced (with respect to HSV wild type). Advantageously, the capability of the modified HSV of binding in specific conditions receptor nectin1/HveC is substantially ablated.

According to some preferred embodiments, the capability of the modified HSV of binding in specific conditions receptor HVEM/HveA is reduced, advantageously substantially ablated.

The illustrative embodiments are disclosed using as an exemplary virus a member of the Herpesviridae family, HSV-1.

HSV-1 and HSV-2 are herpes simplex viruses. The subject matter of the present invention extends to any member of the Herpesviridae family and is not limited to the exemplary embodiments disclosed in the examples. Many HSV are known in the art. Such viruses may contain one or more mutated genes. Examples of recombinant viruses containing heterologous gene and methods of making and using such viruses are described in U.S. Pat. No. 5,599,691. Heterologous genes include genes encoding marker proteins (such as red or green fluorescent proteins or variations thereof, luciferase or β-galactosidase), which allow detection of infected cells expressing the protein.

The modified HSV herein provided has the advantage of maintaining a relevant part of the infectivity of the wild type virus.

According to specific embodiments, the peptide ligand is inserted in gD (glycoprotein D) of the glycoproteic envelope of HSV. A portion of gD is de peptide ligand is inserted in place of the deleted portion, in particular, so that the peptide ligand and gD form a fusion protein.

Usually, (mature) wild type gD has the peptide sequence SEQ ID NO:1.

Wild type gD derives from a precursor, which has peptide sequence SEQ ID NO:34.

The mentioned precursor is codified by the nucleotide sequence SEQ ID NO:35.

According to some embodiments of the present invention, gD, before it is modified, has at least 50%, 60%, 70%, 80%, 85%, 90%, 95% or 100% homology, advantageously identity, with respect to SEQ ID NO:1.

According to some embodiments, the portion, which extends between positions corresponding to 40 to 61 SEQ ID NO:46, on the one side, and 210 to 218 SEQ ID NO:47, on the other side, is deleted. Advantageously, the deleted portion extends between positions corresponding to 61, on the one side, and 218, on the other side.

Herein, loci (positions) of the peptide sequences modified or non-modified are identified with reference to a aminoacid numbering of aminoacid residues in corresponding positions of a unmodified (mature) wild type gD as identified by SEQ ID NO:1. Corresponding positions may be identified by aligning the unmodified residues (see above). For example, we hereinafter report the numbering of sequences of wild type gD (SEQ ID NO:1) and its precursor (SEQ ID NO:34)

receptor, which has at least 70%, 80%, 90%, 95% or 100% homology, advantageously identity, with respect to receptor HER2/ErbB2.

HER2/ErbB2 is a receptor which is overexpressed by, e.g., ovary tumor, mammary tumor, stomach tumor and salivary glands tumor cells (Hynes N. E. and H. A. Lane. "ERBB receptors and cancer: the complexity of targeted inhibitors." Nat Rev Cancer (2005) 5: 341; Holbro, T. & Hynes, N. E. ErbB receptors: directing key signaling networks throughout life. Annu. Rev. Pharmacol. Toxicol. 44, 195-217 (2004); Hynes, N. E. & Stern, D. F. The biology of erbB-2/neu/HER-2 and its role in cancer. Biochim. Biophys. Acta 1198, 165-184 (1994)), and which is expressed at very low levels in non malignant tissues (Yamamoto et al; Nature. 1986 Jan. 16-22;319(6050):230-4) (Press M. F et al., Oncogene (1990) 5:953).

According to other embodiments, the peptide ligand is capable of binding in specific conditions the given receptor, which has at least 70%, 80%, 90%, 85% or 100% homology, advantageously identity, with respect to a given receptor chosen in the group consisting of: EGFR1 (epidermal growth factor receptor1) [Carpenter, G. (1992). Receptor tyrosine kinase substrates: src homology domains and signal transduction. *Faseb J* 6(14), 3283-9], EGFR3 [Hynes, N. E., and Lane, H. A. (2005). ERBB receptors and cancer: the complexity of targeted inhibitors. *Nat Rev Cancer* 5(5), 341-54], PMSA (antigen associated with the prostatic membrane), CEA (car-

```
                                                               SEQ ID NO: 1
KYALADASLK  MADPNRFRGK  DLPVLDQLTD  PPGVRRVYHI  QAGLPDPFQP  PSLPITVYYA    60

VLERACRSVL  LNAPSEAPQI  VRGASEDVRK  QPYNLTIAWF  RMGGNCAIPI  TVMEYTECSY   120

NKSLGACPIR  TQPRWNYYDS  FSAVSEDNLG  FLMHAPAFET  AGTYLRLVKI  NDWTEITQFI   180

LEHRAKGSCK  YALPLRIPPS  ACLSPQAYQQ  GVTVDSIGML  PRFIPENQRT  VAVYSLKIAG   240

WHGPKAPYTS  TLLPPELSET  PNATQPELAP  EDPEDSALLE  DPVGTVAPQI  PPNWHIPSIQ   300

DAATPYHPPA  TPNNMGLIAG  AVGGSLLAAL  VICGIVYWMR  RRTQKAPKRI  RLPHIREDDQ   360

PSSHQPLFY                                                                369
                                                              SEQ ID NO: 34
MGGAAARLGA  VILFVVIVGL  HGVRG

KYALADASLK  MADPNRFRGK  DLPVLDQLTD  PPGVRRVYHI  QAGLPDPFQP  PSLPITVYYA    60

VLERACRSVL  LNAPSEAPQI  VRGASEDVRK  QPYNLTIAWF  RMGGNCAIPI  TVMEYTECSY   120

NKSLGACPIR  TQPRWNYYDS  FSAVSEDNLG  FLMHAPAFET  AGTYLRLVKI  NDWTEITQFI   180

LEHRAKGSCK  YALPLRIPPS  ACLSPQAYQQ  GVTVDSIGML  PRFIPENQRT  VAVYSLKIAG   240

WHGPKAPYTS  TLLPPELSET  PNATQPELAP  EDPEDSALLE  DPVGTVAPQI  PPNWHIPSIQ   300

DAATPYHPPA  TPNNMGLIAG  AVGGSLLAAL  VICGIVYWMR  RRTQKAPKRI  RLPHIREDDQ   360

PSSHQPLFY                                                                369
```

According to some embodiments, the deleted portion extends between positions corresponding to 1 to 8 SEQ ID NO:44, on the one side, and 38 to 55 SEQ ID NO:45 on the other side. Advantageously, the deleted portion is located between positions corresponding to 6, on the one side, and 38, on the other side.

The aforementioned peptide ligand is any type of suitable ligand known in the art, for example a cytokine, a growth factor, a derivative of monoclonal antibody or, advantageously, a single chain antibody.

According to some specific embodiments, the peptide ligand is capable of binding in specific conditions the given cinoembrional antigen), GD2 (disialoganglioside, expressed in neuroblastoma and in melanoma), VEGF (vascular endothelial growth factor) receptors 1 and 2 expressed in neovasculature [Carmeliet, P. (2005). VEGF as a key mediator of angiogenesis in cancer. Oncology 69 Suppl 3, 4-10].

It is important to stress that, for some of the aforementioned receptors natural ligands are known, e.g EGF, VEGF. In the state of the art, monoclonal antibodies and single chain antibodies, which target receptor expressed by diseased cells, are known. For example, J591, J415 e J533 have been made (see the patent application having publication number US20030007974). Single chain antibodies to EGFR1 (Nakamura, T., Peng, K. W., Vongpunsawad, S., Harvey, M., Mizuguchi, H., Hayakawa, T., Cattaneo, R., and Russell, S. J. (2004). Antibody-targeted cell fusion. *Nat Biotechnol* 22(3), 331-6), to EGFR3 (Horak, E., Heitner, T., Robinson, M. K., Simmons, H. H., Garrison, J., Russeva, M., Furmanova, P., Lou, J., Zhou, Y., Yuan, Q. A., Weiner, L. M., Adams, G. P., and Marks, J. D. (2005). Isolation of scFvs to in vitro produced extracellular domains of EGFR family members. *Cancer Biother Radiopharm* 20(6), 603-13), to VEGFR2/KDR (Δ7 scFv, Boldicke, T., Tesar, M., Griesel, C., Rohde, M., Grone, H. J., Waltenberger, J., Kollet, O., Lapidot, T., Yayon, A., and Weich, H. (2001). Anti-VEGFR-2 scFvs for cell isolation. Single-chain antibodies recognizing the human vascular endothelial growth factor receptor-2 (VEGFR-2/flk-1) on the surface of primary endothelial cells and preselected CD34+ cells from cord blood. *Stem Cells* 19(1), 24-36) have been described.

Single chain antibodies against CEA have been prepared: inter alia, scFv MFE23 (which was disclosed in: Chowdhury et al, Retargeting Retrovirus, 2004 Mol. Ther. 9:85, Imaging, Mayer A., Clin. Cancer. Res. 6 (5): 1711 (2000), and in the patent application having publication number US20020090709) and scFv T84.66 (which was disclosed in: Hu, Cancer Research (1996) 56:3055; Olafsen T. et al., Protein Eng. Des. Sel. (2004) 17:21; Wong Y. J. et al., Clin. Cancer Res. (2004) 10:5014; Kenanova V. et al., Cancer Res. (2005) 65:622; US20030171551). The monoclonal antibody MAb 3F8 (US20040116379, US20040115688, U.S. Pat. No. 6,716,422, Kushner B. H. et al., (2001) 19:4189, Tur M. K. et al., Int. J. Molec. Med. (2001) 8:579, US20040180386) and the single chain antibody scFv 14.18 against GD2 are also known in the art.

According to some specific embodiments, the ligand has at least 70%, 80%, 85%, 901, 951, 100% homology (advantageously identity) with a ligand chosen in the group consisting of scFv J591, scFv MFE23, MAb 3F8, scFv T84.66 and scFv 14.18.

According to some embodiments, the ligand consists of at least three hundred aminoacids; advantageously at least three hundred and twenty, three hundred and sixty or two hundred and forty.

Advantageously, the ligand comprises a first domain (VL) and a second domain (VH) and a first linker (L1), which connects the first and the second domain (VL, VH) and is capable of allowing the first and the second domain (VL, VH) to take an adequate relative position; the first and the second domain (VL, VH) being designed to bind said given receptor.

The ligand further comprises a second linker (L2) and/or a third linker (L3). The second domain (VH) being located between and connecting the first and the second linker (L1, L2). The first domain (VL) being located between and connecting the first and the third linker (L1, L3).

The first domain (VL) consists of at least one hundred aminoacids, advantageously no more than one hundred and seventeen aminoacids. The second domain (VH) consists of at least one hundred and ten, advantageously no more than one hundred and thirty, aminoacids. The first linker (L1) consists of at least twelve, advantageously no more than thirty, amino acids.

According to some embodiments, the first domain (VL) has at least 80%, 90%, 951, 98%, 100% homology, advantageously identity, with respect to SEQ ID NO:2.

```
                                          SEQ ID NO: 2
SDIQMTQSPS SLSASVGDRV TITCRASQDV NTAVAWYQQK

PGKAPKLLIY SASFLYSGVP SRFSGSRSGT DFTLTISSLQ

PEDFATYYCQ QHYTTPPTFG QGTKVEI
```

According to some embodiments, the first domain (VL) has at least 80%, 90%, 95%, 98% or 100% homology, advantageously identity, with respect to SEQ ID NO:3.

```
                                          SEQ ID NO: 3
SEVQLVESGG GLVQPGGSLR LSCAASGFNI KDTYIHWVRQ

APGKGLEWVA RIYPTNGYTR YADSVKGRFT ISADTSKNTA

YLQMNSLRAE DTAVYYCSRW GGDGFYAMDY WGQGTLVTVS
```

According to some embodiments, the first linker (L1) has at least 50%, 60%, 70%, 80%, 90%, 95%, 98% or 100% homology, advantageously identity, with respect to SEQ ID NO:4.

```
KSDMPMADPN RFRGKNLVFH         SEQ ID NO: 4
```

According to some embodiments, the second linker (L2) has at least 50%, 60%, 70%, 80%, 90%, 95%, 98% or 100% homology, advantageously identity, with respect to SEQ ID NO:5 or SEQ ID NO:8.

```
    SSGGGSGSGG S          SEQ ID NO: 5

SSGGGSGSGG SG         SEQ ID NO: 8
```

According to some embodiments, the third linker (L3) consists of at least two and, advantageously, no more than eight aminoacids. The third linker (L3) has at least 50%, 60%, 70%, 80%, 90% or 100% homology, advantageously identity, with respect to SEQ ID or SEQ ID NO:7.

```
        EN                SEQ ID NO: 6

HSSGGGSG          SEQ ID NO: 7
```

According to some particular embodiments, the peptide ligand is inserted in gD (glycoprotein D) of the glycoproteic envelope and a portion of gD is deleted so that the obtained modified gD has at least 70%, 80%, 90%, 95%, 98% or 100% homology, advantageously identity, with respect to SEQ ID NO:10 or SEQ ID NO:9.

```
                                          SEQ ID NO: 10
KYALADASLK MADPNRFRGK DLPVLDQLTD PPGVRRVYHI

QAGLPDPFQP PSLPITVYYA HSSGGGSGSD IQMTQSPSSL

SASVGDRVTI TCRASQDVNT AVAWYQQKPG KAPKLLIYSA

SFLYSGVPSR FSGSRSGTDF TLTISSLQPE DFATYYCQQH

YTTPPTFGQG TKVEIKSDMP MADPNRFRGK NLVFHSEVQL

VESGGGLVQP GGSLRLSCAA SGFNIKDTYI HWVRQAPGKG

LEWVARIYPT NGYTRYADSV KGRFTISADT SKNTAYLQMN

SLRAEDTAVY YCSRWGGDGF YAMDYWGQGT LVTVSSSGGG

SGSGGSGMLP RFIPENQRTV AVYSLKIAGW HGPKAPYTST
```

-continued

```
LLPPELSETP NATQPELAPE DPEDSALLED PVGTVAPQIP

PNWHIPSIQD AATPYHPPAT PNNMGLIAGA VGGSLLAALV

ICGIVYWMRR RTQKAPKRIR LPHIREDDQP SSHQPLFY

SEQ ID NO: 9
KYALAENSDI QMTQSPSSLS ASVGDRVTIT CRASQDVNTA

VAWYQQKPGK APKLLIYSAS FLYSGVPSRF SGSRSGTDFT

LTISSLQPED FATYYCQQHY TTPPTFGQGT KVEIKSDMPM

ADPNRFRGKN LVFHSEVQLV ESGGGLVQPG GSLRLSCAAS

GFNIKDTYIH WVRQAPGKGL EWVARIYPTN GYTRYADSVK

GRFTISADTS KNTAYLQMNS LRAEDTAVYY CSRWGGDGFY

AMDYWGQGTL VTVSSSGGGS GSGGSHIQAG LPDPFQPPSL

PITVYYAVLE RACRSVLLNA PSEAPQIVRG ASEDVRKQPY

NLTIAWFRMG GNCAIPITVM EYTECSYNKS LGACPIRTQP

RWNYYDSFSA VSEDNLGFLM HAPAFETAGT YLRLVKINDW

TEITQFILEH RAKGSCKYAL PLRIPPSACL SPQAYQQGVT

VDSIGMLPRF IPENQRTVAV YSLKIAGWHG PKAPYTSTLL

PPELSETPNA TQPELAPEDP EDSALLEDPV GTVAPQIPPN

WHIPSIQDAA TPYHPPATPN NMGLIAGAVG GSLLAALVIC

GIVYWMRRRT QKAPKRIRLP HIREDDQPSS HQPLFY
```

The precursors of SEQ ID NO:10 and SEQ ID NO:9 may be expressed by SEQ ID NO:36 and SEQ ID NO:37, respectively.

The herein disclosed peptide sequences, in particular the modified gD, may be post-traslationally changed. Possible changes include, but are not limited to glycosylation, pegylation, albumination, farnysylation, carboxylation, hydroxylation, phosphorylation.

In this regard it should be noted that, wild type gD has N-linked oligosaccharides added at every specific consensus sequence (Asn-X-Ser and/or Asn-X-Thr) (Sodora, D. L., G. H. Cohen, and R. J. Eisenberg. 1989. Influence of asparagine-linked oligosaccharides on antigenicity, processing, and cell surface expression of herpes simplex virus type 1 glycoprotein D. J Virol 63:5184-93) and possible O-linked oligosaccharides added at one or more Ser and/or Thr residue. Advantageously, also the modified gD and/or the ligand include such modifications.

It has been experimentally seen that, surprisingly, the modified HSV according to the present invention, although the sequences aa 7-32, that in wt gD are involved in the interaction with HVEM, were not always deleted, has lost not only the ability to interact with nectin1, but also with HVEM, and is therefore detargeted from both natural receptors HVEM and nectin1.

In this regard, it should be noted that, contrary to efforts described by Zhou and Roizman (WO2004/033639), the used ligand (in this-case the scFv) is not inserted at the N-terminus of gD, but is inserted between two portions of gD that contain residues that can not be deleted (namely the N-terminus up to aa residue 60, and the region 218-end). A particular feature of the modified HSV is that these portions are linked together in a single polypeptide chain, and are linked and held together, in particular, by the scFv that, in this case, fulfills simultaneously two functions (i) provides the new ligand for the receptors to be targeted (and hence directs the tropism of the recombinant virus to the receptor of choice), and (ii) provides the scaffolding function that, in wt-gD, is located in the Ig-folded portion included in the polypeptide 61-218.

Further modifications that conceivably improve the ability of the targeted virus to specifically attach to and enter cells that express the receptor targeted by the heterologous ligand include the removal of specific sequences in glycoprotein gB (aminoacid residues 68-77) and gC (aminoacid residues 136-152) that enable the binding to the non specific HSV receptor heparan sulphate. Such sequences, or extensions thereof, may be replaced with the heterologous ligand of choice, in order to concentrate further the recombinant virus on the cells of choice.

A further implementation consists in the introduction in the viral genome of mutations that greatly favour the spread of the virus from an infected cell to a nearby adjacent cells. Mutations that exert such effect are known. Typically they cause the infected cells to form a syncytium (or polykaryocyte) with nearby cells, and are called syncytial (syn) mutations. Examples of such mutations are A40V located in gK and R858H, T813I, R796C located in gB.

In accordance with a further aspect of the present invention, there is provided the above identified modified HSV for use as a medicament, advantageously for treating tumors; in particular, ovary tumor, mammary tumor, prostate tumor, colon tumor, stomach tumor, salivary gland tumor, melanoma, neuroblastoma, head and neck carcinoma, neoangiogenic tissue, in particular neoangiogenic tissues of a tumor, and/or metastasis thereof. Advantageously, the above defined modified HSV is used for treating ovary tumor, mammary tumor, prostate tumor, stomach tumor, salivary gland tumor and metastasis thereof. Advantageously, the above defined modified HSV is provided for use in treating ovary tumor, mammary tumor and metastasis thereof.

In this regard, it is important to point out that the aforementioned modified HSV is particularly useful for treating tumor metastasis. This is due to the fact that once the modified HSV is administered, it diffuses and infects autonomously the metastasis.

The modified HSV may be administered to a subject by any known means. In particular, the modified HSV may be administered directly in the area of a tumor or, alternatively, systemically, for example where metastasis have been detected or the tumor is not directly accessible.

Pharmaceutical preparations containing the modified HSV are substantially devoid of impurities that may cause damages to the subject, in particular human beings or other mammals. Pharmaceutical preparations, advantageously, comprise one or more pharmaceutically acceptable excipients.

The modified HSV may be formulated for every known type of administration: in particular, for oral or parenteral or rectal administration or in forms designed for inhalation or insufflation (both by mouth and by nose). Formulation for parenteral use are advantageous.

For oral administration, the pharmaceutical preparations can be, for example, in the form of tablets or capsules prepared using known methods with excipients acceptable from a pharmaceutical point of view as binding agents (for example pre-gelatised corn starch, polyvinylpyrrolidone or methylcellulose); fillers (for example lactose, microcrystalline cellulose or calcium hydrogen phosphate); additives (for example magnesium stearate, talc, silica); disintegrants (for example potato starch); and/or lubricating agents (for example sodium lauryl sulphate). The tablets can be coated with known methods. Liquid preparations for oral administration may have the form, for example, of syrupy solutions or suspensions, or they can be in the form of a dry product which can be dissolved in water or in another liquid before use. These preparations can be prepared in known ways with pharmaceutically acceptable additives such as-suspending agents (for example sorbitol, cellulose derivatives, edible hydrogenated fats); emulsifying agents (for example lecithin or acacia); non aqueous liquids (for example almond oil, oily esters, ethyl alcohol or fractionated vegetable oils); and/or preservatives (for example methyl or propylp-hydroxybenzoates, sorbic acid or ascorbic acid). The preparations can also contain, in appropriate cases, buffering salts, colouring, aromatic and/or sweetening agents.

Preparations for oral administration can be formulated in a known way, so as to give a controlled release of the active compound.

The modified HSV can be formulated, in a known way, for parenteral administration by injection or continuous administration. Formulae for injection may be in the form of single doses, for example in ampoules or multidose containers containing preservatives. The preparation may be in the form of a suspension, in aqueous or oily liquids, and it may contain formulation elements such as dispersing and stabilising agents. Alternatively, the active compound may be in powder form to be dissolved immediately before use in a suitable liquid, for example sterilised water.

The modified HSV can be formulated for rectal administration as suppositories or enteroclysis, for example containing excipients for suppositories of a known type such as cocoa butter or other fats.

The modified HSV can also be formulated, in a known way, as preparations with prolonged release. These preparations with prolonged release can be administered by means of an implant (for example subcutaneous, or intramuscular) or by means of an intramuscular injection. So, for example, the modified HSV can be formulated with suitable polymeric or hydrophobic materials (for example an emulsion or an oil) or resins with ionic exchange, or relatively poorly soluble derivatives, such as relatively poorly soluble salts.

For intranasal administration, the modified HSV can be formulated for administration by means of a (known) device, for example in powder form with a suitable carriers.

The dosages of the modified HSV may be defined as the number of plaque forming unit (pfu). Example of dosages include $10^3$, $10^4$, $10^5$, $10^6$, $10^7$, $10^8$, $10^9$, $10^{10}$, $10^{11}$ pfu.

The subject to be treated may be any mammal, for example a human being. Other examples of animals that may be treated are: farm animals such as cattle, swine, goat, sheep, horse; pets such as cats and dogs; rabbit, mouse, rat.

In some cases it is possible to administer the modified HSV together with further treatments of chemi-, immuno-, radiotherapy and/or other types of treatments.

In particular, the modified HSV may be used in combination with inhibitors of angiogenesis such as, for example: Endostatine (EntreMED), SU5416, SU6668 B (Sugen, San Francisco), Talidomide, COL-3 (Collagenex, Newton, Pa.), AG3340 (Agouron, LaJolla, Calif.), Marimastat (British Biotech), Neovastat (Aeterna, Quebec), BMS-275291 (Bristol-Myers Squibb).

In accordance with a further aspect of the present invention, there is provided the use of a modified HSV for visualising a physiological condition, advantageously for identifying tumor metastasis. Accordingly, it is herein provided the use of the modified HSV for preparing a composition for visualising a physiological condition. Such a composition may be prepared using known methods so that it can be administered to a subject.

Advantageously, the visualization may be directed to: ovary tumor, mammary tumor, prostate tumor, colon tumor, stomach tumor, salivary gland tumor, melanoma, head and neck carcinoma, neoangiogenic tissue, in particular neoangiogenic tissues of a tumor, and neuroblastoma and/or metastasis thereof; advantageously, ovary tumor, mammary tumor, prostate tumor, stomach tumor, salivary gland tumor and metastasis thereof; in particular, ovary tumor, mammary tumor and metastasis thereof.

The visualization of physiological conditions may be obtained by means of imaging of the expression of the gene thymidine-kinase (TK) using detecting highly sensible techniques such as PET or SPECT (Sharma et al, Molecular imaging of gene expression and protein function in vivo with PET and SPECT, J. Magn. Reson. Imaging., 16(4):336-51, 2002) (Vries et al., Scintgraphic Imaging of HSV Gene Therapy, Curr. Pharm. Des., 8(16):1435-50, 2002) (Vries et al., Positron Emission Tomography: measurement of transgene expression, Methods, 27(3):234, 2002).

Alternatively it is possible to fuse a non-essential protein (for example $U_s11$) and a reporter protein capable of being identified in vivo (for example red or green fluorescent proteins or variations thereof, luciferase or β-galactosidase).

Where the luciferase is used, its presence may be emphasized by means of a suitable luminescent or chromatic substrate. The reporter protein may be fused to a thymidine-kinase (Soling et al., Intercellular localization of Herpes simplex virus of the type 1 thymidine kinase fused to different fluorescent proteins depends on choice of fluorescent tag, FEBS Lett., 527(1-3):153, 2002).

In accordance with a further aspect of the present invention, there is provided a process of preparing a modified HSV as above defined. The process comprises an insertion phase, during which a nucleotide sequence codifying the peptide ligand is inserted in the DNA of HSV so that the so obtained modified HSV expresses on its envelope the peptide ligand.

Advantageously, the DNA of the HSV is so manipulated that the gD codifying sequence of the modified HSV has at least 70%, 80%, 90%, 95% or 100% homology, advantageously identity, with respect to SEQ ID NO:36 or SEQ ID NO:37, in particular SEQ ID NO:37.

Before insertion suitable ligands, advantageously a single chain antibodies, may be identified using known techniques for testing their ability of binding at least one receptor expressed by the diseased cells.

Further characteristics of the present invention will be clarified the following description of some merely illustrative and non-limiting examples.

EXAMPLE 1

Construction of HSV Expressing Genetically Modified gDs Carrying Deletions Substituted with a Single Chain Antibody Directed to HER2/Neu and Carrying EGFP as Reporter Gene A) Deletion of gD from HSV-BAC.

To generate a gDminus virus, the "ET-cloning" procedure in bacteria was performed (Muyrers, J. P., Y. Zhang, G. Testa, and A. F. Stewart. 1999. Rapid modification of bacterial artificial chromosomes by ET-recombination. Nucleic Acids Res 27:1555-7). A kanamycin resistance cassette flanked by two FRT sites was PCR amplified from the plasmid pFRT-2, with primers that contained at their 5' ends 60 nt of sequences flanking gD ORF: gDup_Kan_f (TGT TCG GTC ATA AGC TTC AGC GCG AAC GAC CAA CTA CCC CGA TCA TCA GTT ATC CTT AAG CCA GTG AAT TCG AGC TCG GTA C) (SEQ ID NO:11) and gDdown_Kan_r (ACT TAT CGA CTG TCC ACC TTT CCC CCC TTC CAG ACT CGC TTT ATA TGG AGT TAA GGT CCC GAC CAT GAT TAC GCC AAG CTC C) (SEQ ID NO:12). pFRT-2 was constructed by insertion of the kanamycin resistance derived from pCP15 into the NsiI sites of pCP16 replacing the tetracyclin resistance gene Cherepanov, P. P., and W. Wackernagel. 1995. Gene disruption in *Escherichia coli:* TcR and KmR cassettes with the option of Flp-catalyzed excision of the antibiotic-resistance determinant. Gene 158:9-14. The PCR product was electroporated into DH10B *E. coli* (Stratagene) harboring the YEbac102 HSV-BAC Tanaka, M., H. Kagawa, Y. Yamanashi, T. Sata, and Y. Kawaguchi. 2003. Construction of an excisable bacterial artificial chromosome containing a full-length infectious clone of herpes simplex virus type 1: viruses reconstituted from the clone exhibit wild-type properties in vitro and in vivo. J Virol 77:1382-91, and transiently expressing lambda phage Red-β and Red-γ recombinases from pKD46 plasmid. Datsenko, K. A., and B. L. Wanner. 2000. one-step inactivation of chromosomal genes in *Escherichia coli* K-12 using PCR products. Proc Natl Acad Sci USA 97:6640-5. Recombinant clones were selected on plates containing two antibiotics, 25 µg/ml kanamycin (the marker contained in the PCR product) and 20 µg/ml chloramphenicol (the marker contained into HSV-BAC sequences), to ensure substitution of the gD coding sequence by the kanamycin resistance cassette. To remove the kanamycin cassette, the positive clones were electroporated with pCP20 (Cherepanov, P. P., and W. Wackernagel. 1995. Gene disruption in *Escherichia coli:* TcR and KmR cassettes with the option of Flp-catalyzed excision of the antibiotic-resistance determinant. Gene 158:9-14), a plasmid expressing yeast FLP recombinase, which targets FRT sequences. Finally the colonies were assayed for loss of the kanamycin marker and for chloramphenicol resistance. The resulting gDminus HSV-BAC genome, designated 102gD⁻FRT, was checked by Southern blot, PCR, sequencing, and for the ability to form plaques only in R6, and not in other cell lines.

B) Engineering of EGFP (Enhanced Green Fluorescent Protein) or LacZ Reporter Genes into 102gD⁻FRT HSV-BAC.

The second step in the engineering of HSV-BAC recombinants was the insertion of the reporter gene EGFP or LacZ, thus generating gDminus-EGFP-HSV-BAC or gDminus-LacZ-HSV-BAC. We chose as site of reporter gene insertion the pBeloBAC sequences themselves, so that, the marker gene can be deleted together with the BAC sequences by Cre recombinase, if required (FIG. 1A). The coding sequence of EGFP followed by the polyadenylation signal from the bovine growth hormone (BGH) was PCR amplified from pCMS-EGFP (Clontech) with primers EGFP_BamHI_f (CAA CCC GGG ATC CAC CGG TCG CCA CCA TGG TGA GC) (SEQ ID NO:13) and EGFP+pA_BamHI_r (CCC CTT GGG ATC CTG CCC CAC CCC ACC CCC CAG AAT AG) (SEQ ID NO:14), and cloned downstream the HSV a27 promoter. The a27-EGFP cassette was inserted between two 700 by sequences, PCR amplified from the plasmid pBeloBac11 (GenBank Accession #: U51113). The two aforementioned 700 by sequences were designated as pBeloBac11-up [primers Sal_pBelo_1209_f: TTG CCA GTC GAC ATT CCG GAT GAG CAT TCA TCA GGC GGG CA (SEQ ID NO:15) and pBelo_1897_Xho_r: GCA AAA ACT CGA GTG TAG ACT TCC GTT GAA CTG ATG GAC (SEQ ID NO:16)] and pBeloBac11-down [primers Mun_pBelo_1898_f: GGA AGT CAA TTG GAA GGT TTT TGC GCT GGA TGT GGC TGC CC (SEQ ID NO:17) and pBelo_2586_Eco_r: CAC ACT GAA TTC GCA ATT TGT CAC AAC ACC TTC TCT AGA AC (SEQ ID NO:18)]. In the resulting construct, the a27-EGFP cassette resulted inserted between nt 1897 and 1898 (original coordinates) of pBeloBac11. The cassette a27-EGFP plus the pBeloBac11 flanking sequences was subcloned in the shuttle vector pST76KSR Adler, H., M. Messerle, M. Wagner, and U. H. Koszinowski. 2000. Cloning and mutagenesis of the murine gammaherpesvirus 68 genome as an infectious bacterial artificial chromosome. J Virol 74:6964-74 for homologous recombination in bacteria. For LacZ insertion, we followed the same strategy, cloning pBeloBac11-up and -down sequences into a plasmid already containing the a27-LacZ cassette. The relevant insert and adjacent regions were sequenced for accuracy in all plasmids.

C) Construction of Shuttle Vectors for Insertion of Chimeric gD into gDminus BACs.

Figure 8:
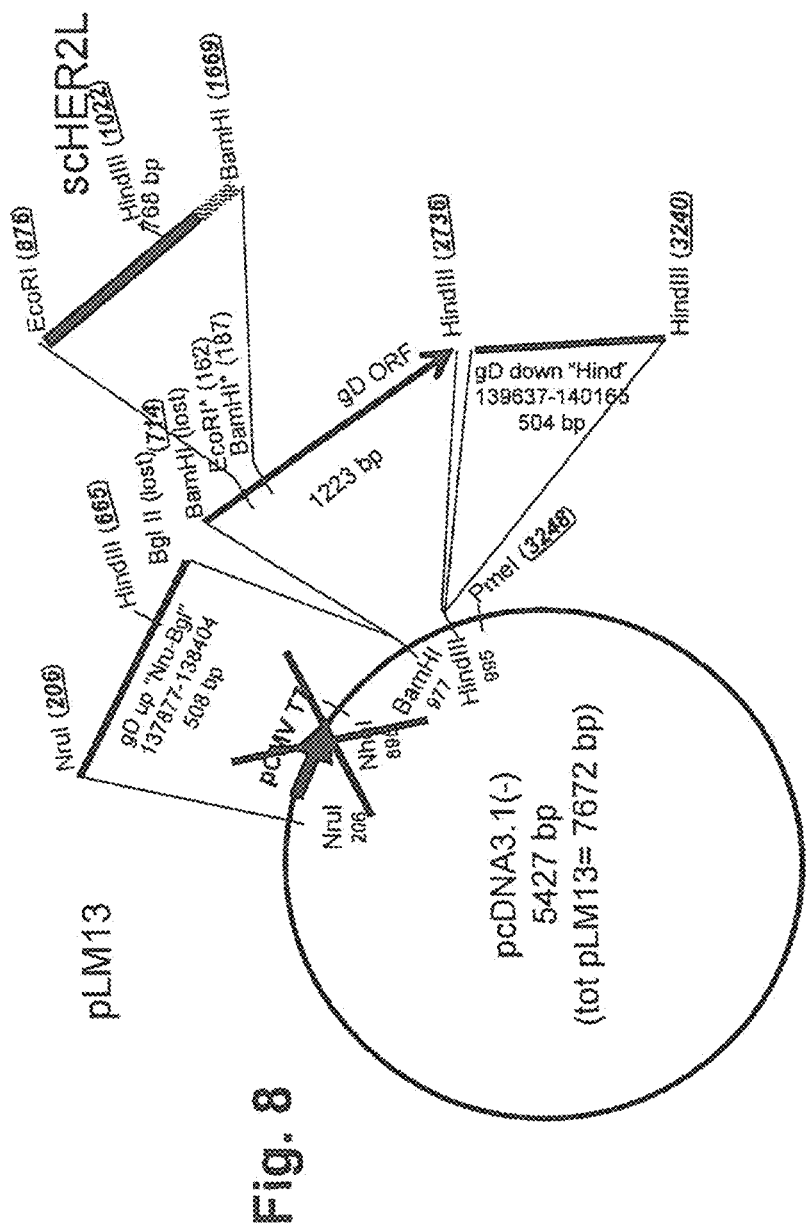
Figure 9:
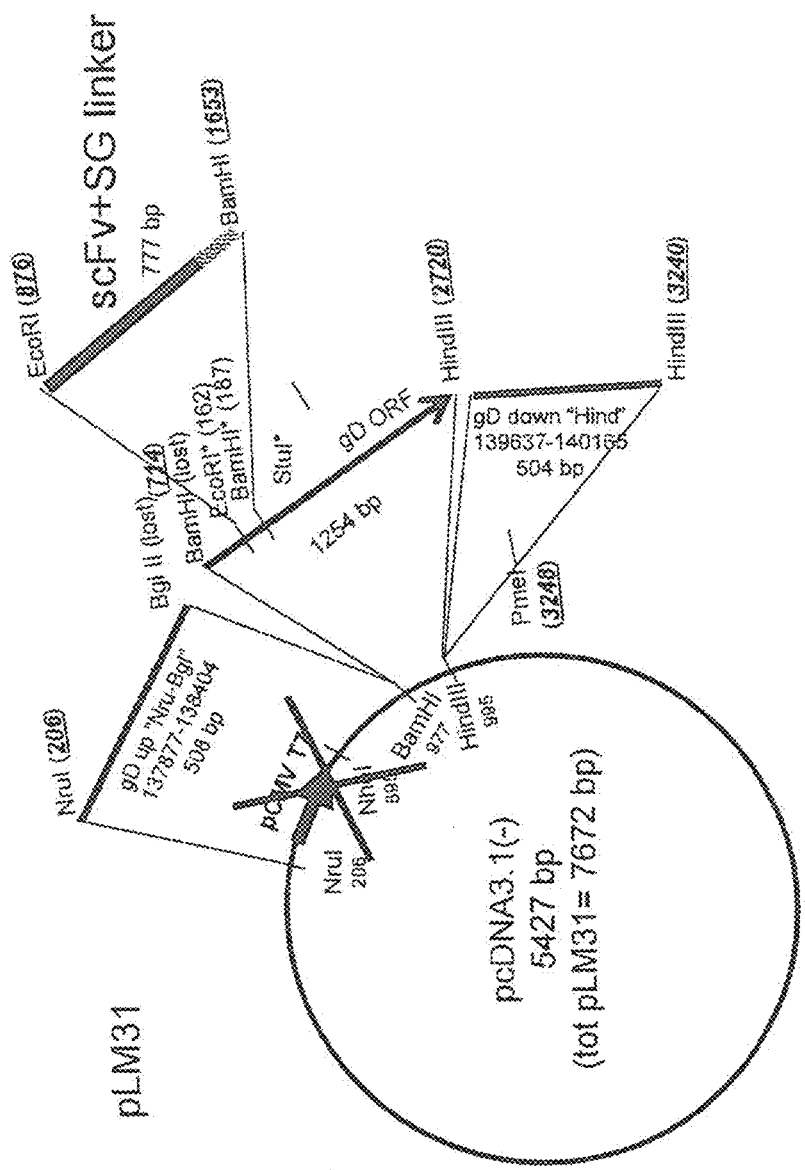
Figure 10:
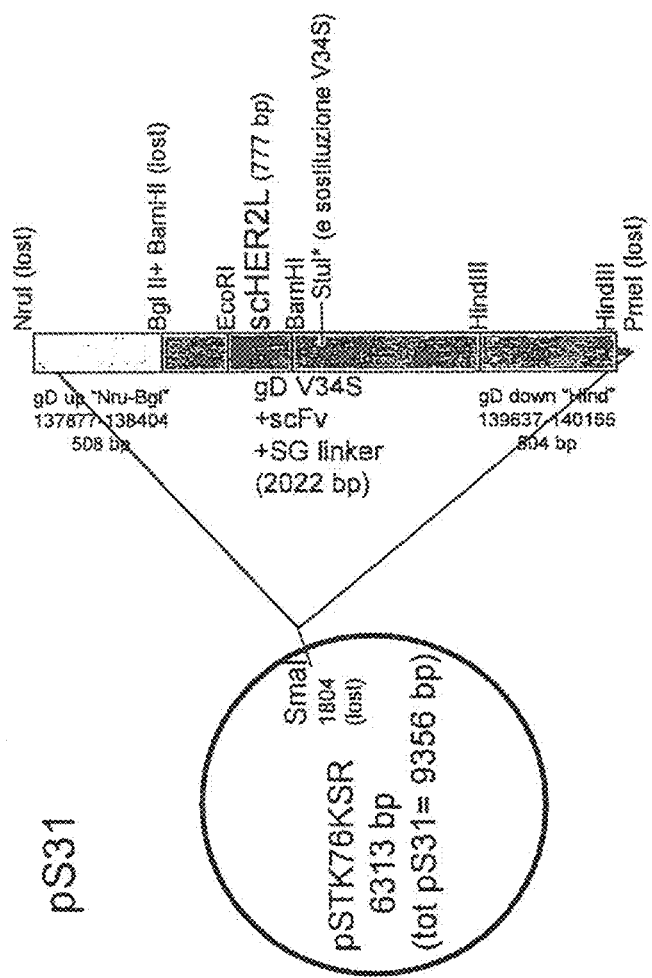

The gD shuttle vector named pS31 (FIG. 10) carries the scHER2L (scFv anti HER2 plus a 9-aa serine glycine Linker) inserted between aa residues 24 and 25 of gD, plus the V34S substitution (FIG. 1B, b). It was constructed as follows. First, the V34S substitution was introduced by site directed mutagenesis in pLM13 (FIG. 8), a construct carrying scHER2L inserted between aa residues 24 and 25 of gD, generating pLM31 (FIG. 9). Mutagenesis was performed by means of the Stratagene Quickchange II kit (Stratagene) with primers gD_34S_StuI 5'-TCC TCC GGG GAG CCG GCG CGT GTA CCA CAT CCA GGC AGG CCT ACC GG-3' (SEQ ID NO:19) and its reverse. The primers contained the indicated silent restriction sites, for ease of mutant clones screening. Next, the cassette containing the mutagenized gD+scHER2 plus gD genomic upstream and downstream flanking sequences (about 500 by each) was transferred to pST76KSR shuttle vector to enable homologous recombination in *E. coli.*

Figure 11:
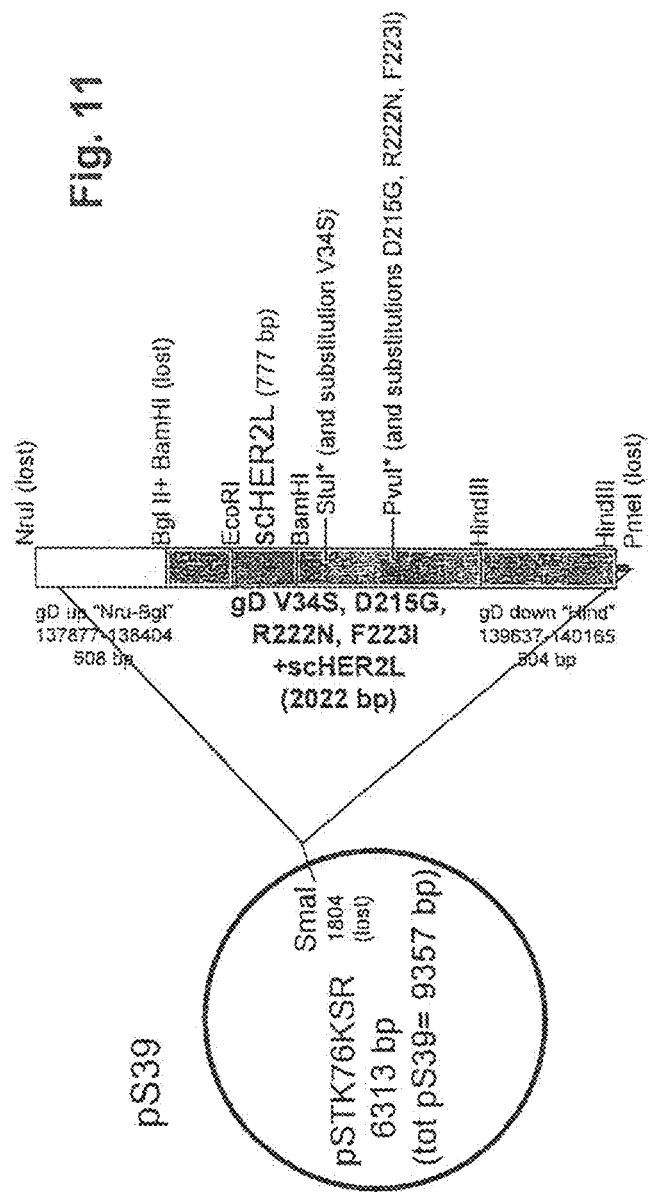

To construct pS39 (FIG. 11), the D215G, R222N, F223I substitutions were added to gD cloned in pS31 by means of the primer gD_215G-222N-223I_PvuI 5'-AGG GGG TGA CGG TGG GCT CGA TCG GGA TGC TGC CCA ACA TCA TCC CCG AGA ACC-3' (SEQ ID NO:20) and its reverse (FIG. 1B, c).

Figure 7:
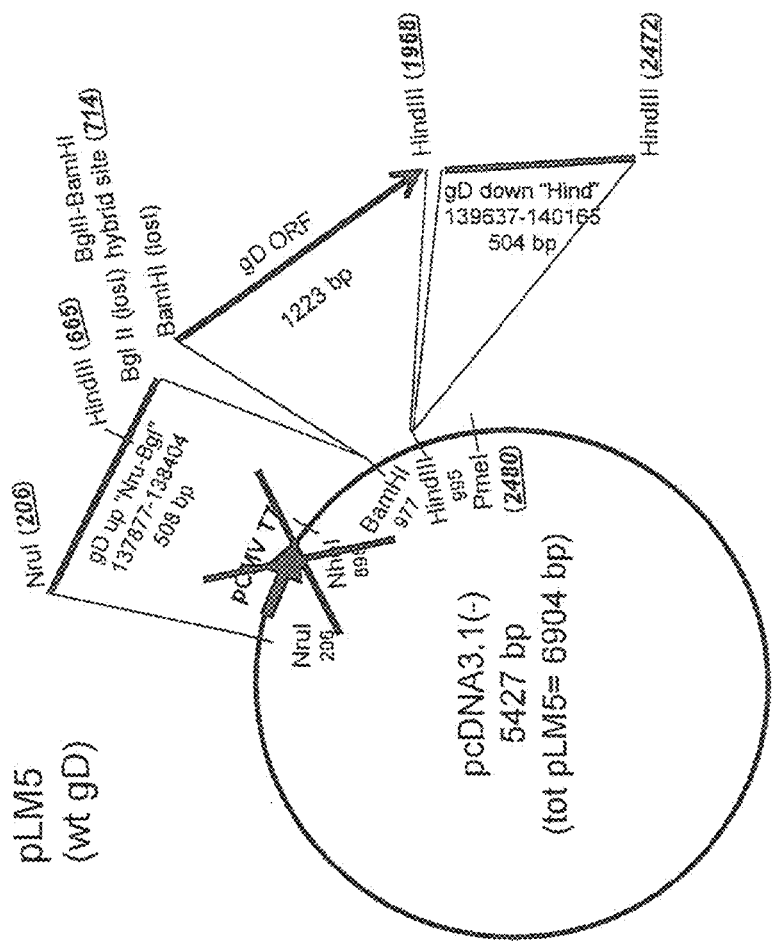
FIGS. 7 to 15 show maps of the following plasmids: pLM5, pLM13 (scHER2L between aa 24 and 25 of mature gD), pLM31 (obtained by mutagenesis of pLM13 to introduce the V34S substitution), pS31 (shuttle plasmid obtained by subcloning of the NruI-PmeI fragment from pLM31 into SmaI of pST76KSR), pS39 (shuttle plasmid obtained by mutagenesis of pS31 with primer gD_215G-222N-223I_PvuI), pLM113 (carries the sequence coding gD where aa 6-38 of the mature protein are replaced by scHER2L), pS113 (shuttle plasmid obtained by subcloning of the NruI-PmeI fragment from pLM113 into SmaI of pST76KSR), pLM249 (carries the sequence coding gD where aa 61-218 of the mature protein are replaced by scHER2 flanked by linkers), pS249 (shuttle plasmid obtained by subcloning of the NruI-PmeI fragment from pLM249 into SmaI of pST76KSR), respectively: underlined bold italic numbers indicate coordinates in the final complete plasmid; plain font numbers indicate coordinates in original vector and fragments.
Figure 12:
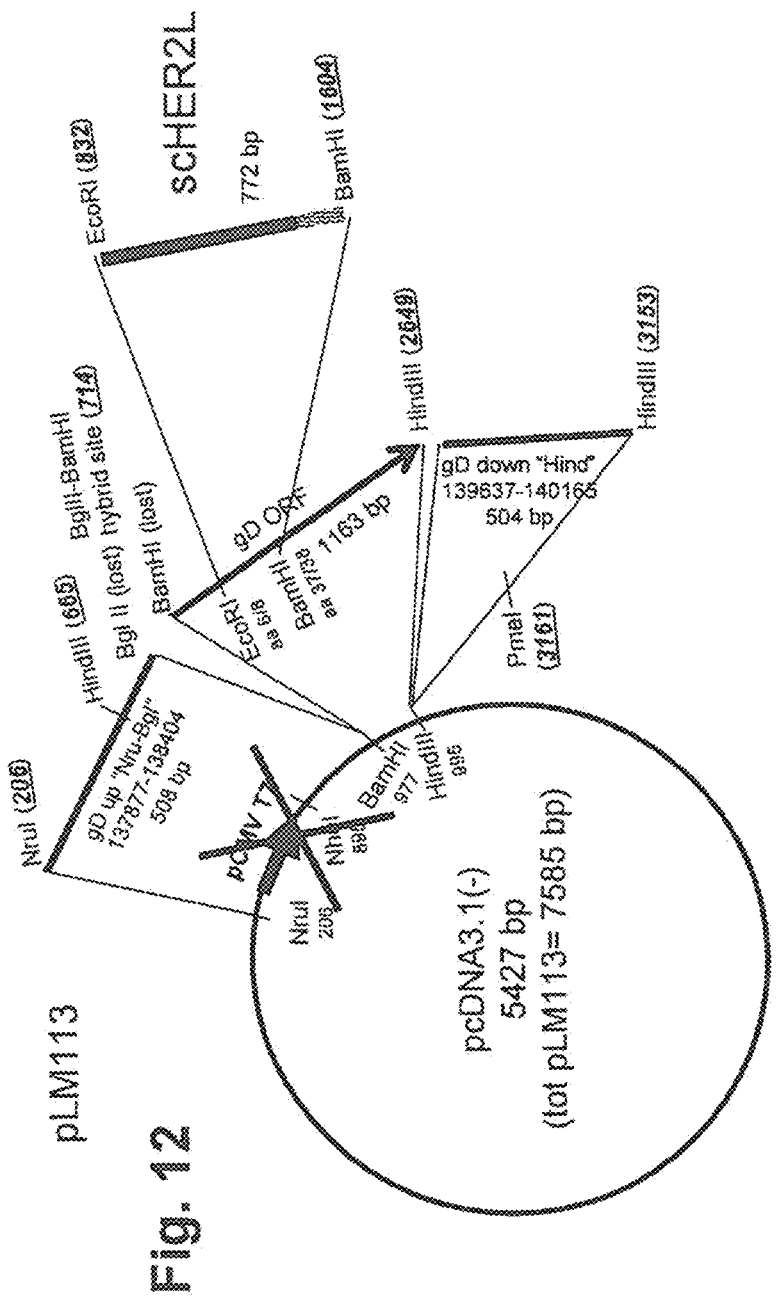
Figure 13:
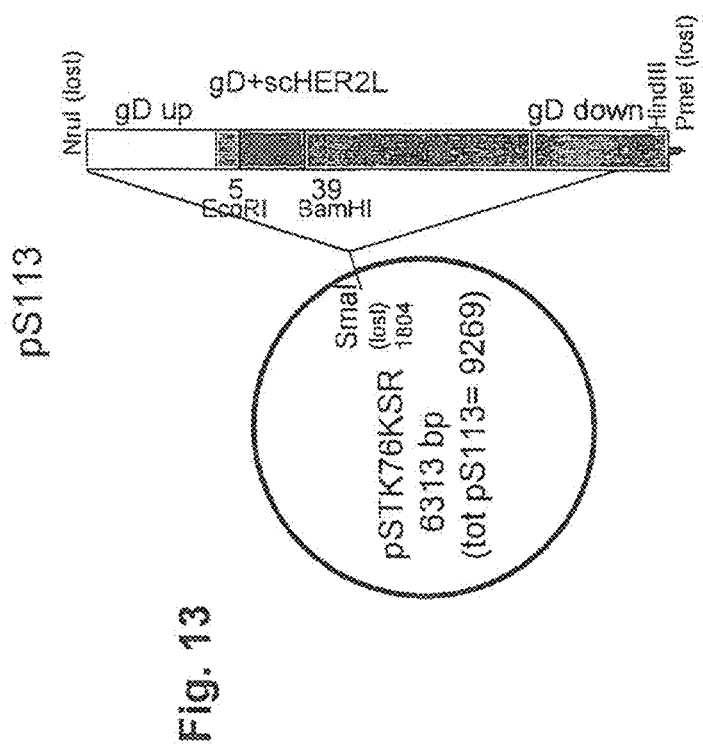

The pS113 shuttle vector (FIG. 13) contains gD, in which aa residues 6-38 were deleted and replaced with scHER2L [scFv anti HER2 followed by a 11 aa serine-glycine linker: SSGGGSGSGGS (SEQ ID NO:5), encoded by the sequence TCGAGTGGCGGTGGCTCTGGTTCCGGTGGATCC (SEQ ID NO:21)] (FIG. 1B, d). To generate this construct, EcoRI and BamHI restriction sites were sequentially introduced in gD ORF in pLM5 (FIG. 7). The EcoRI restriction site was inserted in the aminoacid positions 6-8 of the protein sequence and BamHI restriction site was inserted in the amino acid positions 37-39 of the protein sequence, by means of the mutagenic primers gD_6/8_EcoRI_f 5'-CAA ATA TGC CTT GGC GGA GAA TTC TCT CAA GAT GGC CG-3' (SEQ ID NO:22) and gD_37/38_BamHI_f 5'-CGG GGG TCC GGC GCG GAT CCC ACA TCC AGG CGG G-3' (SEQ ID NO:23), respectively. The insertion of the EcoRI site introduces the substitutions D6E and A7N. The scHER2L was amplified from pS2019a Sidhu, S. S., B. Li, Y. Chen, F. A. Fellouse, C. Eigenbrot, and G. Fuh. 2004. Phage-displayed antibody libraries of synthetic heavy chain complementarity determining regions. J Mol Biol 338:299-310 with primers scFv_x6_Eco_f 5'-GCA AAG GAA TTC CGA TAT CCA GAT GAC CCA GTC CCC G-3' (SEQ ID NO:24) and scFv_SG_x37_BamH 5'-CGG AGG ATC CAC CGG AAC CAG AGC CAC CGC CAC TCG AGG-3' (SEQ ID NO:25). This construct was designated pLM113 (FIG. 12). The final shuttle plasmid pS113 was constructed by subcloning the engineered gD along with genomic flanking sequences (NruI-PmeI fragment) into pST76KSR (FIG. 13).

Figure 14:
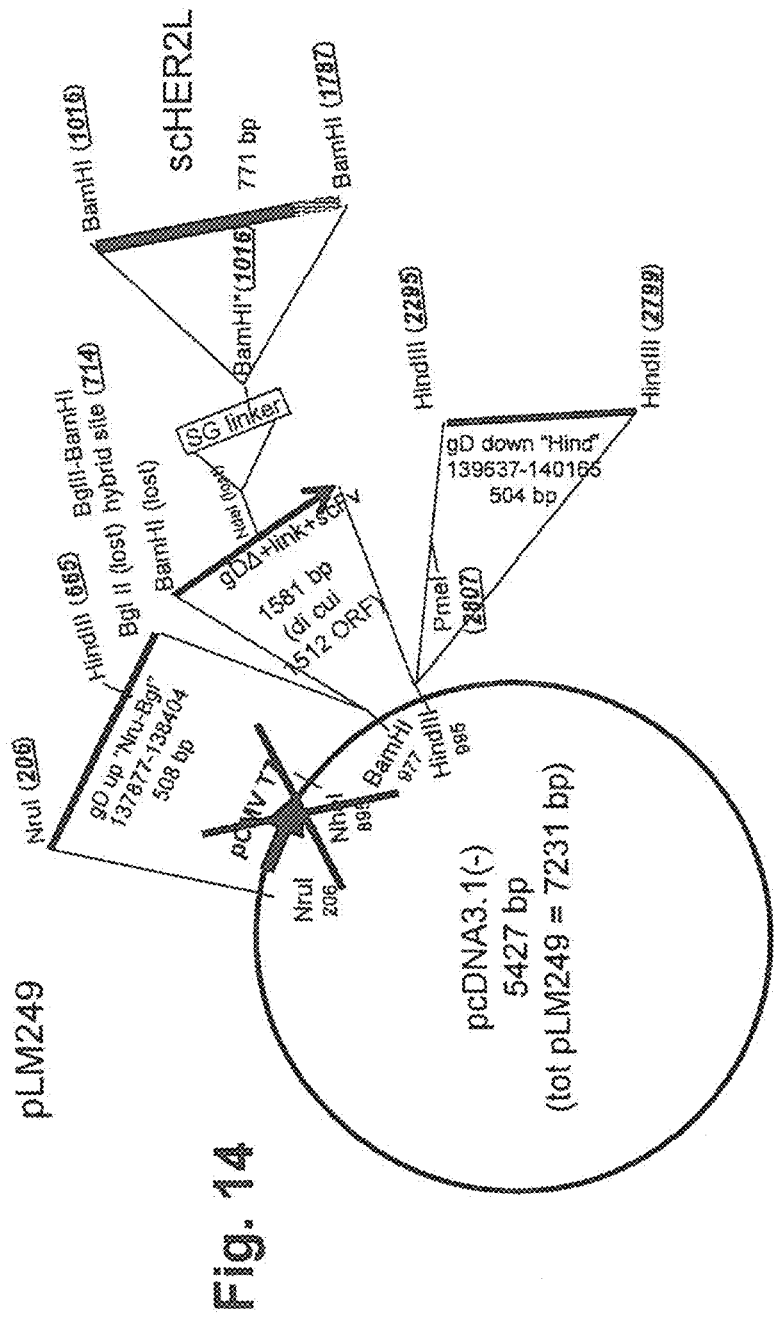
Figure 15:
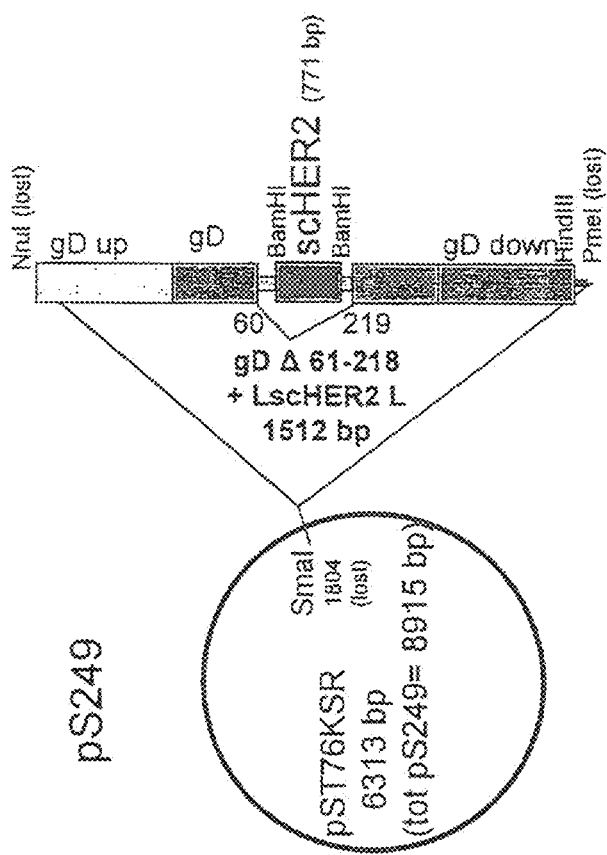

The pS249 shuttle vector contains gD, in which aa residues 61-218 were deleted and replaced with LscHER2L [scFv anti HER2 flanked by serineglycine linkers, upstream 8 aa: HSSGGGSG (SEQ ID NO:7), encoded by the sequence CAT-AGTAGTGGCGGTGGCTCTGGA (SEQ ID NO:26); downstream 12 aa: SSGGGSGSGGSG (SEQ ID NO:8), encoded by the sequence TCGAGTGGCGGTGGCTCTG-GTTCCGGTGGATCCGGT (SEQ ID NO:27)] in place of gD aa residues 61 to 218 (FIG. 1B, e). Mutagenesis and cloning was performed on pLM5 (FIG. 7), a plasmid containing gD ORF cloned in pcDNA3.1(−) (Invitrogen), flanked by two 500-bp upstream and downstream genomic flanking sequences 15' Menotti, L., A. Cerretani, and G. Campadelli-Fiume. 2006. A herpes simplex virus recombinant that exhibits a single-chain antibody to HER2/neu enters cells through the mammary tumor receptor, independently of the gD receptors. J Virol 80:5531-9. First, two NdeI sites were inserted in the coding sequence replacing the amino acids 61-62 and 218-219 of mature gD, respectively, by using mutagenic primers gD_61/62_NdeI_f (5'-acg gtt tac tac gcc CAT Atg gag cgc gcc tgc c-3') (SEQ ID NO:28) and gD_218/219_NdeI_f (5'-GAC GGT GGA CAG CAT CCA TAT GCT GCC CCG CTT C-3') (SEQ ID NO:29). Next, a 9 aa serine-glycine linker was inserted by annealing and ligating into the NdeI site the two phosphorylated oligos P-SG9Bam7/Nde_f (5'-TAG TAG TGG CGG TGG CTC TGG ATC CGG-3') (SEQ ID NO:30) and P-SG9Bam7/Nde_r (5'-tAC CGG AtC CAG AGC CAC CGC CAC Tac-3') (SEQ ID NO:31), containing a silent BamHI site. The scHER2 was amplified from pS2019a Sidhu, S. S., B. L1, Y. Chen, F. A. Fellouse, C. Eigenbrot, and G. Fuh. 2004. Phage-displayed antibody libraries of synthetic heavy chain complementarity determining regions. J Mol Biol 338:299-310 with primers scFv_Bam_f (5'-GGC TTA TGG ATC CGA TAT CCA GAT GAC CCA GTC CCC-3') (SEQ ID NO:32) and scFv_SG_x37_BamH_r (5'-CGG Agg atc cAC CGG AAC CAG AGC CAC CGC CAC TCG AGG-3') (SEQ ID NO:33) and inserted into the BamHI site of the serine-glycine linker. The total insert length is of 801 bp, encoding 267 aa residues. The construct was designated pLM249. Finally the cassette containing the engineered gDA61-218+fscHER2L plus gD genomic upstream and downstream flanking sequences (the NruI-PmeI fragment from pLM249) was subcloned into SmaI of pST76KSR shuttle vector generating pS249 (FIG. 14) for homologous recombination in *E. coli*. The relevant insert and adjacent regions were sequenced for accuracy in all plasmids.

D) Generation of recombinant genomes by two-step replacement in bacteria. The procedure applied to generate recombinant genomes in *E. coli* was essentially as described, with slight modifications O'Connor, M., M. Peifer, and W. Bender. 1989. Construction of large DNA segments in *Escherichia coli*. Science 244:1307-12; Messerle, M., I. Crnkovic, W. Hammerschmidt, H. Ziegler, and U. H. Koszinowski. 1997. Cloning and mutagenesis of a herpesvirus genome as an infectious bacterial artificial chromosome. Proc Natl Acad Sci USA 94:14759-63; Borst, E. M., G. Hahn, U. H. Koszinowski, and M. Messerle. 1999. Cloning of the human cytomegalovirus (HCMV) genome as an infectious bacterial artificial chromosome in *Escherichia coli*: a new approach for construction of HCMV mutants. J Virol 73:8320-9. Briefly, electrocompetent DH10B *E. coli* (Stratagene) harbouring the relevant gDminus HSV-BAC genomes were electroporated with the shuttle vector in 0.2 cm electroporation cuvettes (Bio-Rad) at 200 O, 25 µF, 2.5 kV, plated on LB agar containing 25 µg/ml Kana (the shuttle vector's marker) and 20 µg/ml Cam (the BAC's marker Tanaka, M., H. Kagawa, Y. Yamanashi, T. Sata, and Y. Kawaguchi. 2003. Construction of an excisable bacterial artificial chromosome containing a full-length infectious clone of herpes simplex virus type 1: viruses reconstituted from the clone exhibit wild-type properties in vitro and in vivo. J Virol 77:1382-91), and incubated at 30° C. o/n to allow the expression of RecA from the shuttle vector. The clones were re-plated onto LB+Kana+Cam at 43° C. to allow the identification of those harbouring the cointegrates (visible as large colonies, as compared to the temperature sensitive "small colony" phenotype determined by non-integrated shuttle vectors). Subsequently, the cointegrates were allowed to resolve by plating the clones onto LB+Cam at 30° C., and clones containing the resolved HSV-BAC were selected on LB+Cam plates supplemented with 10% sucrose. Finally, the clones were checked for loss of Kana resistance, and for the presence of the desired insert by colony PCR.

Recombination between the 102gD⁻FRT HSV-BAC and the appropriate shuttle vectors generated gDminus-EGFP-HSV-BAC, or gDminus-LacZ-HSV-BAC DNAs, that contain the a27promoter-EGFP (or a27promoter-LacZ) cassette inserted into the BAC sequences (FIG. 1A). The viruses were reconstituted by transfection of the BAC DNA in the gD-complementing R6 cells.

The gDminus-HSV-BACs was used as recipient for the generation of recombinants containing the engineered gD. The recombinant genomes were checked by PCR and sequencing. The viruses were reconstituted by transfection of the BAC-DNAs into R6 cells Zhou, G., V. Galvan, G. Campadelli-Fiume, and B. Roizman. 2000. Glycoprotein D or J delivered in trans blocks apoptosis in SK-N-SH cells induced by a herpes simplex virus 1 mutant lacking intact genes expressing both glycoproteins. J Virol 74:11782-91, followed by a single passage in BHK (baby hamster kidney) cells, and subsequent growth in J-HER2 Menotti, L., A. Cerretani, and G. Campadelli-Fiume. 2006. A herpes simplex virus recombinant that exhibits a single-chain antibody to HER2/neu enters cells through the mammary tumor receptor, independently of the gD receptors. J Virol 80:5531-9 or SKOV3 (ATCC #HTB-77) cells. The virus stocks were grown in J-HER2 or SKOV3 cells and serially passaged for more than 10 passages. The virus titer was determined in SKOV3 cells.

EXAMPLE 2

Infection Assay with the R-LM31 Recombinant Carrying the V34S Substitution in gD The 1$^{st}$ generation recombinants R-LM11 and R-LM11L carried scHER2 inserted between aa residues 24 and 25 of gD Menotti, L., A. Cerretani, and G. Campadelli-Fiume. 2006. A herpes simplex virus recombinant that exhibits a single-chain antibody to HER2/neu enters cells through the mammary tumor receptor, independently of the gD receptors. J Virol 80:5531-9. The insertion altered the N-terminus such that entry through HVEM was hampered. Entry through nectin1 was maintained Menotti, L., A. Cerretani, and G. Campadelli-Fiume. 2006. A herpes simplex virus recombinant that exhibits a single-chain antibody to HER2/neu enters cells through the mammary tumor receptor, independently of the gD receptors. J Virol 80:5531-9. The first attempt to generate a nectin1-detargeted recombinant consisted in the insertion of the V34S mutation in gD-scHER2 (FIG. 1*b*). When introduced in the IL13-retargeted gD, the V34S substitution strongly decreased entry via nectin1 Zhou, G., and B. Roizman. 2006. Construction and properties of a herpes simplex virus 1 designed to enter cells solely via the IL-13alpha2 receptor. Proc Natl Acad Sci USA 103:5508-13. The recombinant LM31-BAC DNA was generated by homologous recombination in *E. coli*. The recipient genome was gDminus-LacZ-HSV-BAC. The R-LM31 recombinant virus was obtained by transfection of the LM31-BAC DNA in the gD-complementing R6 cells. R-LM31 tropism was assayed in J cells expressing human or murine nectin1, or human HER2, and monitored as β-galactosidase activity. As shown in FIG. 2A-D, the R-LM31 recombinant infected J-nectin1 cells (Cocchi, F., L. Menotti, P. Mirandola, M. Lopez, and G. Campadelli-Fiume. 1998. The ectodomain of a novel member of the immunoglobulin superfamily related to the poliovirus receptor has the attributes of a bonafide receptor for herpes simplex viruses 1 and 2 in human cells. J Virol 72:9992-10002) (via either the human or murine receptor); hence it was not detargeted from nectin1. The result indicates that the effect of the V34S substitution varies depending on the insert present in gD:

EXAMPLE 3

Electrophoretic Mobility of Wt and Chimeric gDs Expressed in SKOV3 Cells

SKOV3 cells were infected with R-LM5 (the peptide sequence of gD of R-LM5 is SEQ ID NO:1, whose precursor is expressed by the nucleotide sequence SEQ ID NO:35), R-LM13 (the peptide sequence of gD of R-LM13 is SEQ ID NO:42, whose precursor is expressed by the nucleotide sequence SEQ ID NO:43), R-LM31 (the peptide sequence of gD of R-LM31 is SEQ ID NO:38, whose precursor is expressed by the nucleotide sequence SEQ ID NO:39), R-LM39 (the peptide sequence of gD of R-LM39 is SEQ ID NO:40, whose precursor is expressed by the nucleotide sequence SEQ ID NO:41), R-LM113 (SEQ ID NO:9) and R-LM249 at an m.o.i of 10 pfu/cell. 24 h later infected cell lysates were separated by SDS-PAGE, transferred to nitrocellulose membranes (Amersham), and visualized by Western blotting with MAb BD80 against gD C-terminal portion of the ectodomain, followed by peroxidase-conjugated anti-mouse IgG and enhanced chemioluminescence (FIG. 2E). In the R-LM31 and R-LM39 recombinants the presence of scHER2L results in a slower migration, as in the R-LM13 prototype virus, as compared to R-LM5 carrying wt-gD. In the R-LM113 recombinant the electrophoretic mobility of chimeric gD is indistinguishable from that of the R-LM13-31-39 recombinants'. In the R-LM249 recombinant, the replacement of 158 aa residues of gD with LscHER2L results in a migration intermediate between wt gD and gD of R-LM113 (where 6-38 aa residues of gD are replaced by scHER2L). R-LM113 produces less gD as R-LM5 or R-LM249, as the corresponding lane needed to be loaded with 10 times as much lysate as compared to R-LM5 or R-LM249 to obtained the signal observed in FIG. 2. This lower production of gD was previously reported for viruses carrying deletion in gD N-terminus Zhou, G., and B. Roizman. 2006. Construction and properties of a herpes simplex virus 1 designed to enter cells solely via the IL-13alpha2 receptor. Proc Natl Acad Sci USA 103:5508-13.

EXAMPLE 4

Infection of an Array of Cells Lines by R-LM113 and R-LM249

Monolayers of an array of cell lines of rodent, simian or human origin were infected at increasing m.o.i, and EGFP reporter gene expression (Clontech) was measured 24 h later by means of a fluorometer. Digital pictures were taken with a Kodak camera connected to a Zeiss Axioplan fluorescence microscope. R-LM113 and R-LM249 infected. J-HER2 cells, but not J cells expressing human nectin1 or murine nectin1 as the sole receptor (FIG. 3). The detargeting from murine nectin1 was confirmed by failure to infect L and NIH-3T3 cells. Human cells were susceptible to R-LM113 and R-LM249, provided that they expressed HER2 at high level (SKOV3). HER2-negative cells, e.g. HEp-2 ATCC #CCL-23, 1-143 $tk^-$ (Post, L. E., and Roizman, B. (1981). A generalized technique for deletion of specific genes in large genomes: alpha gene 22 of herpes simplex virus 1 is not essential for growth. *Cell* 25(1), 227-32. ) and RH4 (rhabdomyosarcoma) cells Ricci, C., L. Landuzzi, I. Rossi, C. De Giovanni, G. Nicoletti, A. Astolfi, S. Pupa, S. Menard, K. Scotlandi, P. Nanni, and P. L. Lollini. 2000. Expression of HER/erbB family of receptor tyrosine kinases and induction of differentiation by glial growth factor 2 in human rhabdomyosarcoma cells. Int J Cancer 87:29-36, were infected to a negligible level. Interestingly, R-LM113 and R-LM249 were specific for human HER2, as they failed to infect the TT12.E2 mouse cell line expressing the rat ortholog of HER2 (neu-NT) De Giovanni, C., G. Nicoletti, L. Landuzzi, A. Astolfi, S. Croci, A. Comes, S. Ferrini, R. Meazza, M. Iezzi, E. Di Carlo, P. Musiani, F. Cavallo, P. Nanni, and P. L. Lollini. 2004. Immunoprevention of HER-2/neu transgenic mammary carcinoma through an interleukin 12-engineered allogeneic cell vaccine. Cancer Res 64:4001-9.

EXAMPLE 5

Virus Replication Assay

J, J-hNectin1, J-HVEM, J-HER2, SKOV3, 1-143 $tk^-$ and HEp-2 cells grown in 12-well plates were, infected with the viruses indicated in FIG. 4 at a m.o.i. of 1 pfu/cell for 90 min at 37° C. Following virus adsorption, the inoculum was removed and the non penetrated virus was inactivated by means of an acid wash (40 mM citric acid, 10 mM KCl, 135 mM NaCl (pH 3)) Brunetti, C. R., R. L. Burke, B. Hoflack, T. Ludwig, K. S. Dingwell, and D. C. Johnson. 1995. Role of mannose-6-phosphate receptors in herpes simplex virus entry into cells and cell-to-cell transmission. J Virol 69:3517-28. Replicate cultures were frozen at the indicated times (3, 24, 48 h) after infection. The viral progeny (intracellular plus extracellular) was titrated in SKOV3 cells.

The growth of R-LM39, R-LM113 and R-LM249 was compared to recombinant virus R-LM5 (encoding wild type gD) and R-LM13 (encoding chimeric gD-scHER2L without further mutations or deletions). (i) R-LM39 was unable to grow in J-HVEM cells, but replicated in J-HER2 and in J-nectin1 cells, implying that it could use both HER2 and nectin1 as receptors (FIG. 4B, C, D). Accordingly, it replicated in the human cell lines SKOV3 (that express both nectin1 and HER2), 1-143 $tk^-$ and HEp-2 cells (that express nectin1) (FIG. 4E, F, (ii) R-LM113 grew efficiently in J-HER2 cells, better than R-LM249 and R-LM5 (FIG. 4D). In SKOV3 cells R-LM113 and R-LM249 replicated to titers only 1 to 1.5 orders of magnitude lower than those of the control virus R-LM5 (FIG. 4E). (iii) R-LM113 and R-LM249 were detargeted from both nectin1 and HVEM, as assessed by its inability to grow in J-nectin1 and in J-HVEM cells, as well as in the human 1-143 $tk^-$ and HEp-2 to titers higher than $10^2$-$10^3$-$10^4$ pfu/ml (FIG. 4B, C F, G).

EXAMPLE 6

Inhibition of Virus Infection by Antibodies

SKOV3 cells grown in 96-well plates were incubated for 2 h on ice with increasing concentrations of antibodies (R1.302 to nectin1, Herceptin to HER2, or mouse immunoglobulins) diluted in DMEM without serum, and then with the viral inoculum at the m.o.i of 2 pfu/cell (as titered in SKOV3 cells) for further 90 min on ice. Following virus adsorption, the unattached virus was removed and cells were washed twice with ice cold RPMI+Glutamax supplemented with 2.5% FBS. Cells were overlaid with medium containing the same concentration of antibodies or IgGs, rapidly shifted at 37° C., and incubated for 16 h. Infection was quantified as. EGFP fluorescence intensity by means of a Victor plate reader (Perkin Elmer). The 100% value represents data obtained with cells infected with virus, in the absence of antibodies.

Figure 5:
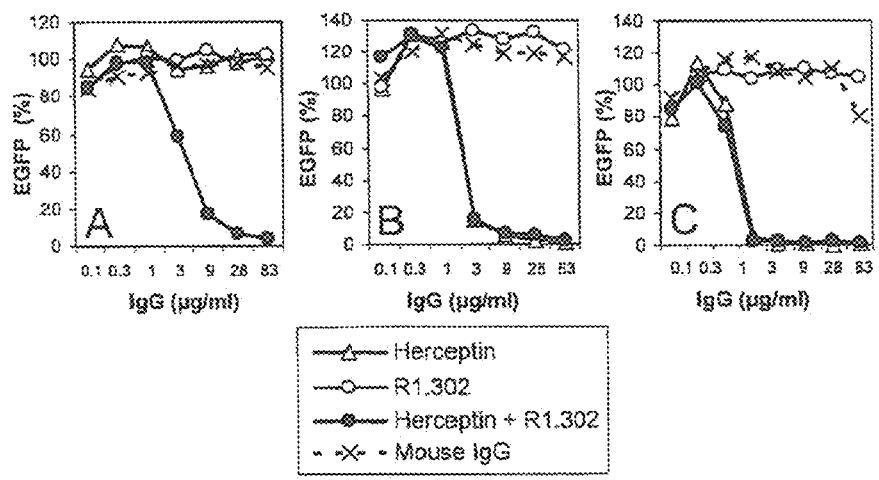
FIG. 5 shows the block of infection of SKOV3 cells with R-LM39 (A), R-LM113 (B) or R-LM249 (C) by antibodies to HER2 (Herceptin) or nectin1 (R1.302). SKOV3 cells were preincubated with the indicated concentrations of purified IgG from Herceptin (Δ), R1.302 (○) or the combination of Herceptin plus R1.302 (●) or irrelevant mouse IgGs (×) for 2 h at 4° C. Virus was added to the antibody containing medium and allowed to adsorb to the cells for 90 min at 4° C. Infection was monitored 16 h later as EGFP expression. One hundred percent indicates the EGFP readings in untreated virus-infected cultures.
Figure 4:
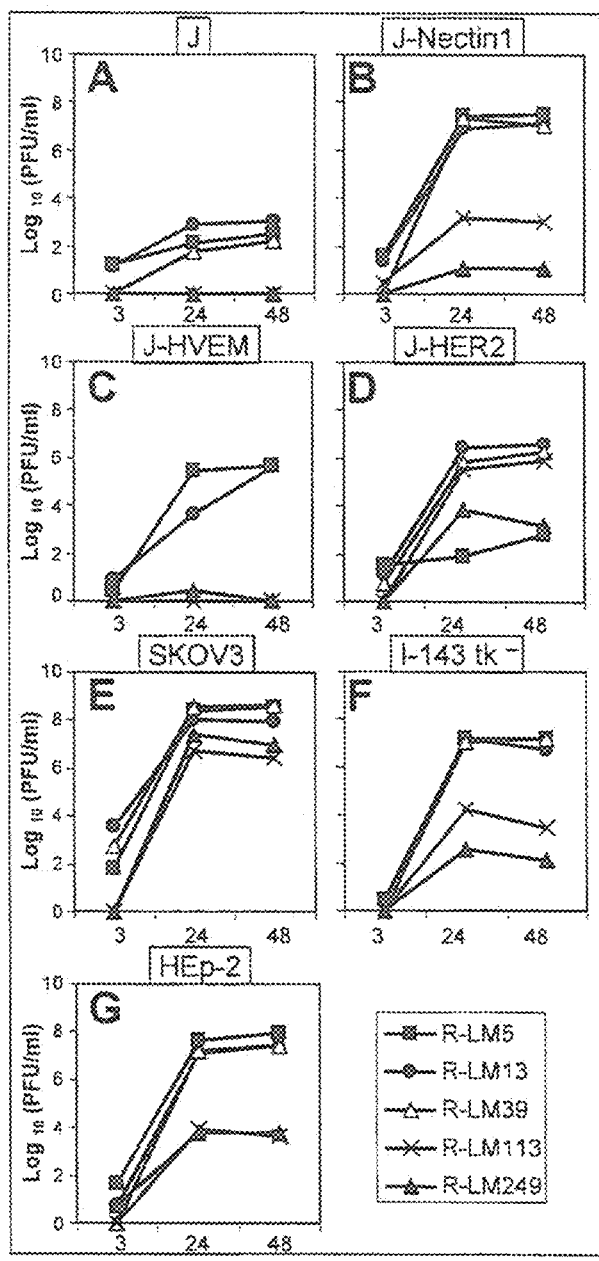
FIG. 4 shows the growth of R-LM39, R-LM113 and R-LM249 recombinants and of control viruses R-LM5 and R-LM13. (A to G) Replicate cultures of J (A), J-Nectin1 (B), J-HVEM (C), J-HER2 (D), SKOV3 (E), 1-143 tk⁻ (F), or HEp-2 (G) cells were infected with recombinant viruses R-LM5 (■), R-LM13 (●), R-LM39 (Δ), R-LM113 (×) or R-LM249 (▲) at 1 PFU/cell. Progeny virus was harvested at 3, 24, and 48 h after infection and titrated in SKOV3 cells.

Receptor usage was confirmed in virus blocking experiments with Herceptin, MAb R1.302, or mixture of the two antibodies. The results in FIG. 5 show that R-LM39 was not blocked by Herceptin or R1.302 administered singly, but only by the two antibodies in combination (FIG. 5A). The results imply that R-LM39 can use alternatively nectin1 or HER2 as receptors, further documenting the lack of detargeting from nectin1. On the contrary R-LM113 and R-LM249 were blocked by Herceptin (FIGS. 5B and C). The combination of Herceptin plus MAb R1.302 exerted the same inhibition as Herceptin alone; MAb R1.302 had no effect. R-LM113 or R-LM249 infection was inhibited by Herceptin alone, while MAb R1.302 alone had no effect. We conclude that R-LM113 and R-LM249 can enter cells only through the HER2 receptor, in accordance with the results shown in FIG. 4.

EXAMPLE 7

Inhibition of R-LM113 and R-LM249 Plaque Formation by Herceptin

Figure 6:
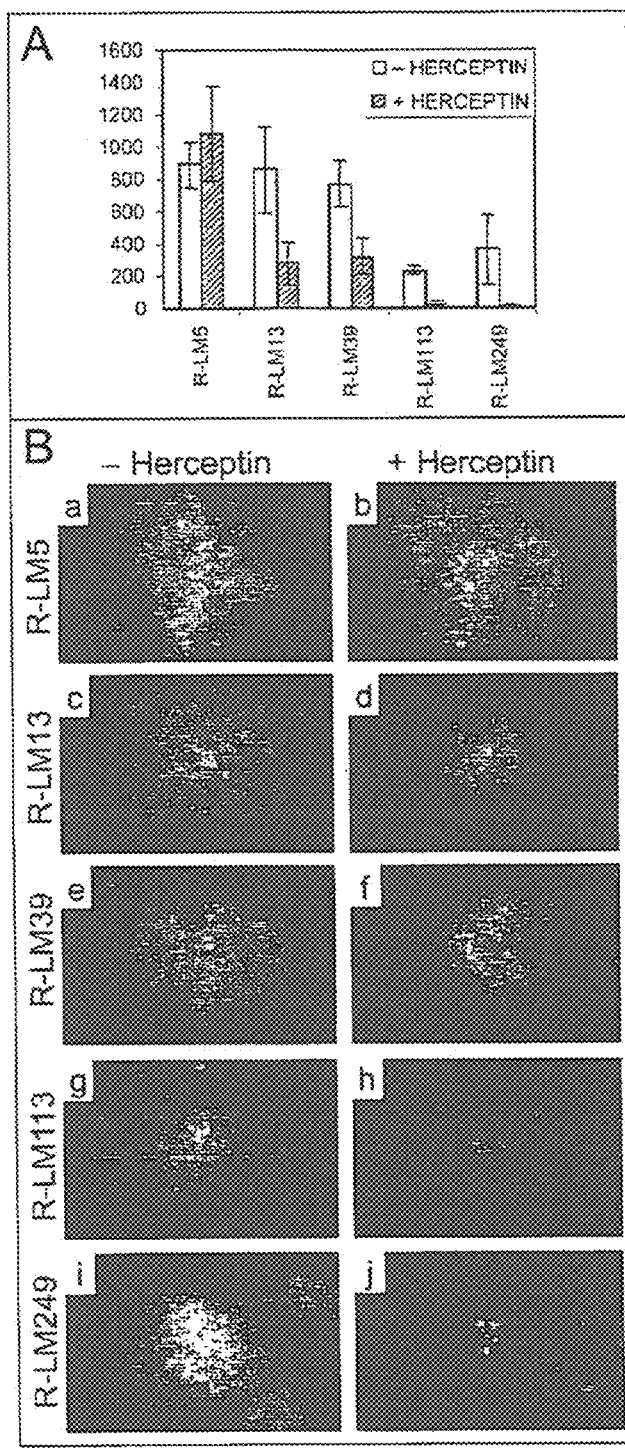
FIG. 6A shows inhibition of cell-to-cell spread by Herceptin. SKOV3 cells infected with serial dilutions of the indicated viruses were overlaid with medium containing with 1% Seaplaque Agarose±10 μg/ml Herceptin. Individual plaques were photographed at 48 h, and the plaque areas were measured by means of the Photoshop Histogram tool program and expressed as pixels×$10^3$. For each virus, the areas of 4 or 5 plaques were measured. Histograms represent averages; error bars, standard deviations.
FIG. 6B shows representative plaques referred to with regard to FIG. 6A.

We asked whether R-LM113 and R-LM249 used HER2 not only for virus infection, but also for cell-to cell spread. SKOV3 cells were infected with serial dilutions of the indicated viruses and overlaid with medium containing 1% Seaplaque agarose, with or without the addition of 10 μg/ml Herceptin (MAb to HER2 Genentech). Fluorescent plaques were monitored with a Zeiss fluorescence microscope, and pictures of 5 plaques per sample were taken at 48 h after infection. The areas of the plaques were measured with Photoshop Histogram tool. As shown in FIG. 6, exposure of R-LM113- and R-LM249-infected SKOV3 monolayers to Herceptin reduced plaque size (in FIG. 6, −Herceptin indicates in the absence of Herceptin; +Herceptin indicates in the presence of Herceptin. Plaque size of R-LM5 and of the other non-detargeted viruses (R-LM13 and R-LM39) was not reduced by Herceptin.

EXAMPLE 8

Cytotoxic Activity of the Recombinant Viruses

Figure 16:
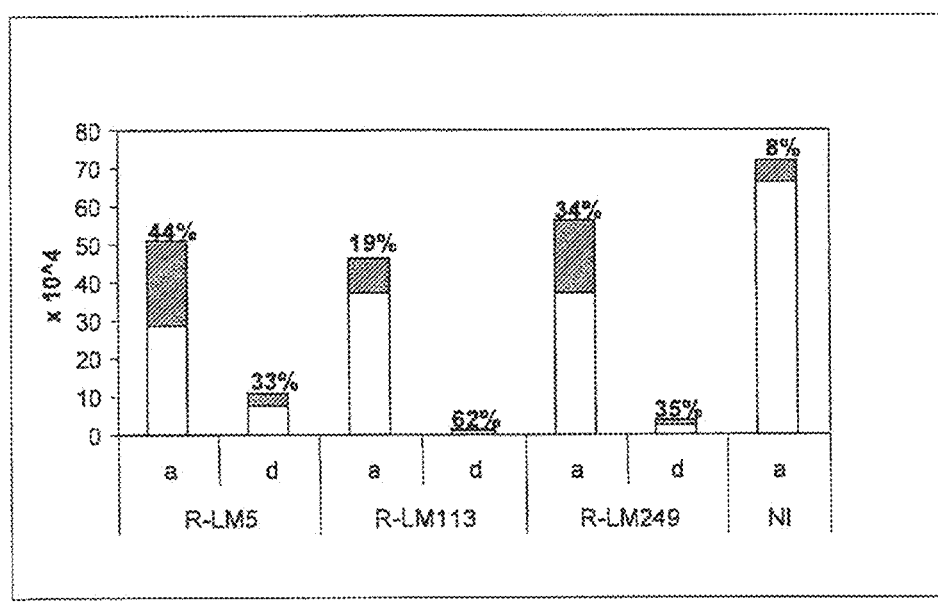
FIG. 16 shows the cytotoxic activity of R-LM113 and R-LM249 recombinants compared to R-LM5 control virus. Histograms represent the the total numbers of cells (y axis: cell number×$10^4$). For each sample of infected, cells both the adherent (a) and detached (d) fractions of cells were counted. The hatched parts of the histograms represent the fraction of nonviable cells (Erythrosin B positive), and the corresponding values are indicated in the percentage values over the histograms. NI, non infected control cells.

We asked whether R-LM113 and R-LM249 maintained the cytotoxic activity of HSV-1 parental virus. SKOV3 cells were seeded in well plates ($4 \times 10^5$ cells/well) and infected the following day with R-LM5, R-LM116 or R-LM249 at a m.o.i. of 3 pfu/cell. After three days the infected cells were trypsinized, and the number of viable and nonviable cells was determined by means of the Erythsosin B exclusion assay. Briefly, cells were mixed 1:1 with 0.04% Erythrosin B (Sigma) in PBS, loaded on a hemocytometer and counted. Nonviable cells take up the stain and appear red in color. The number of nonviable cells was reported as a fraction of the total number of cells (red plus colorless). Cells detached from the monolayer and present in the supernatant of the infected samples were collected and counted in the same way. Replicate wells of non infected cells were included as control. As shown FIG. 16, viral infection almost prevents cells from dividing, as the total number of cells is lower as compared to non infected cells. Moreover infection causes cell cytotoxicity, as the percentage of nonviable cells is higher in infected cultures with respect to non infected replicate cultures. The effect of infection of the R-LM113 and R-LM249 recombinants is comparable to that of R-LM5 virus, carrying wild type gD, indicating that the retargeting and detargeting of the virus did not affect the cytotoxic properties of the recombinants.

The invention claimed is:

1. A modified herpes simplex virus (HSV) comprising a modified glycoprotein envelope; wherein said modified glycoprotein envelope comprises an altered HSV glycoprotein D (gD), wherein said gD has a portion deleted and a single chain antibody inserted thereto;
    wherein the deleted portion (i) starts at any of amino acid residue positions 1 to 8 and ends at any of amino acid residue positions 38 to 55, or (ii) starts at any of amino acid residue positions 40 to 61 and ends ay any of amino acid residue positions 210 to 218;
    wherein the positions of said residues corresponds to the residue numbering of SEQ ID NO: 1.

2. The modified HSV according to claim 1, wherein the deleted portion of gD (i) starts at amino acid residue position 6 and ends at amino acid residue position 38, or (ii) starts at amino acid residue position 61 and ends at amino acid residue position 218.

3. The modified HSV according to claim 1, wherein the single chain antibody binds to the receptor HER2/ErbB2.

4. The modified HSV according to claim 1, wherein the single chain antibody is capable of binding a receptor selected from the group consisting of: EGFR1, EGFR3, PSMA, CEA, GD2, VEGFR1 and VEGFR2.

5. The modified HSV according to claim 1, wherein the single chain antibody comprises a variable light chain (VL) and a variable heavy chain (VH) and a first linker (L1) which is located between and connects VH and VL; or the single chain antibody comprises a second linker (L2) attached to VH, wherein VH is located between and connecting L1 and 2.

6. The modified HSV according to claim 5, wherein the single chain antibody further comprises a third linker (L3); the VL being located between and connecting the first and the third linker (L1, L3).

7. The modified HSV according to claim 5, wherein the VL comprises SEQ ID NO:2 and the VH comprises SEQ ID NO:3.

8. The modified HSV according to claim 5, wherein the first linker (L1) has at least 50% identity with SEQ ID NO:4.

9. The modified HSV according to claim 5, wherein the second linker (L2) has at least 50% identity with respect to SEQ ID NO:5.

10. The modified HSV according to claim 6, wherein the third linker (L3) is selected from the group consisting of: a peptide sequence having at least 50% identity with respect to SEQ ID NO:6 and a peptide sequence having at least 50% identity with respect to SEQ ID NO:7.

11. The modified HSV according to claim 1, wherein the altered gD consists of SEQ ID NO: 10 or SEQ ID NO:9.

12. The modified HSV according to claim 1, wherein the modified HSV further comprises a detectable marker.

13. A medicament comprising the modified HSV according to claim 1.

14. A method for treating tumorigenic cells expressing the receptor HER2/ErbB2, comprising administering to a patient in need thereof an effective amount of the modified HSV of claim 7.

15. A method for detecting cells expressing the receptor HER2/ErbB2 comprising administering the modified HSV of claim 12 to the cells.

16. A pharmaceutical composition comprising a modified HSV according to claim 1, and a pharmaceutical acceptable excipient.

17. A method for preparing the modified HSV of claim 1, the method comprising:
  a) deleting a portion of gD; wherein the deleted portion (i) starts at any of amino acid residue positions 1 to 8 and at any of amino acid residue positions 38 to 55, or (ii) starts at any of amino acid residue positions 40 to 61 and ends at any of amino acid residue positions 210 to 218;
  wherein the positions of said residues corresponds to the residue numbering of SEQ ID NO: 1;
  b) inserting a nucleotide sequence encoding a single chain antibody into the deleted region of the gD following step a), thus generating the modified HSV.

\* \* \* \* \*

SEQUENCE LISTING

```
<160> NUMBER OF SEQ ID NOS: 47

<210> SEQ ID NO 1
<211> LENGTH: 369
<212> TYPE: PRT
<213> ORGANISM: herpes simplex virus

<400> SEQUENCE: 1

Lys Tyr Ala Leu Ala Asp Ala Ser Leu Lys Met Ala Asp Pro Asn Arg
1               5                   10                  15

Phe Arg Gly Lys Asp Leu Pro Val Leu Asp Gln Leu Thr Asp Pro Pro
            20                  25                  30

Gly Val Arg Arg Val Tyr His Ile Gln Ala Gly Leu Pro Asp Pro Phe
        35                  40                  45

Gln Pro Pro Ser Leu Pro Ile Thr Val Tyr Tyr Ala Val Leu Glu Arg
    50                  55                  60
```

```
Ala Cys Arg Ser Val Leu Leu Asn Ala Pro Ser Glu Ala Pro Gln Ile
 65                  70                  75                  80

Val Arg Gly Ala Ser Glu Asp Val Arg Lys Gln Pro Tyr Asn Leu Thr
                 85                  90                  95

Ile Ala Trp Phe Arg Met Gly Gly Asn Cys Ala Ile Pro Ile Thr Val
            100                 105                 110

Met Glu Tyr Thr Glu Cys Ser Tyr Asn Lys Ser Leu Gly Ala Cys Pro
            115                 120                 125

Ile Arg Thr Gln Pro Arg Trp Asn Tyr Tyr Asp Ser Phe Ser Ala Val
        130                 135                 140

Ser Glu Asp Asn Leu Gly Phe Leu Met His Ala Pro Ala Phe Glu Thr
145                 150                 155                 160

Ala Gly Thr Tyr Leu Arg Leu Val Lys Ile Asn Asp Trp Thr Glu Ile
                165                 170                 175

Thr Gln Phe Ile Leu Glu His Arg Ala Lys Gly Ser Cys Lys Tyr Ala
            180                 185                 190

Leu Pro Leu Arg Ile Pro Pro Ser Ala Cys Leu Ser Pro Gln Ala Tyr
        195                 200                 205

Gln Gln Gly Val Thr Val Asp Ser Ile Gly Met Leu Pro Arg Phe Ile
210                 215                 220

Pro Glu Asn Gln Arg Thr Val Ala Val Tyr Ser Leu Lys Ile Ala Gly
225                 230                 235                 240

Trp His Gly Pro Lys Ala Pro Tyr Thr Ser Thr Leu Leu Pro Pro Glu
                245                 250                 255

Leu Ser Glu Thr Pro Asn Ala Thr Gln Pro Glu Leu Ala Pro Glu Asp
            260                 265                 270

Pro Glu Asp Ser Ala Leu Leu Glu Asp Pro Val Gly Thr Val Ala Pro
        275                 280                 285

Gln Ile Pro Pro Asn Trp His Ile Pro Ser Ile Gln Asp Ala Ala Thr
290                 295                 300

Pro Tyr His Pro Pro Ala Thr Pro Asn Asn Met Gly Leu Ile Ala Gly
305                 310                 315                 320

Ala Val Gly Gly Ser Leu Leu Ala Ala Leu Val Ile Cys Gly Ile Val
                325                 330                 335

Tyr Trp Met Arg Arg Arg Thr Gln Lys Ala Pro Lys Arg Ile Arg Leu
            340                 345                 350

Pro His Ile Arg Glu Asp Asp Gln Pro Ser Ser His Gln Pro Leu Phe
        355                 360                 365

Tyr

<210> SEQ ID NO 2
<211> LENGTH: 107
<212> TYPE: PRT
<213> ORGANISM: Artificial
<220> FEATURE:
<223> OTHER INFORMATION: single chain antibody

<400> SEQUENCE: 2

Ser Asp Ile Gln Met Thr Gln Ser Pro Ser Ser Leu Ser Ala Ser Val
  1               5                  10                  15

Gly Asp Arg Val Thr Ile Thr Cys Arg Ala Ser Gln Asp Val Asn Thr
                 20                  25                  30

Ala Val Ala Trp Tyr Gln Gln Lys Pro Gly Lys Ala Pro Lys Leu Leu
             35                  40                  45
```

```
Ile Tyr Ser Ala Ser Phe Leu Tyr Ser Gly Val Pro Ser Arg Phe Ser
    50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln His Tyr Thr Thr Pro
                85                  90                  95

Pro Thr Phe Gly Gln Gly Thr Lys Val Glu Ile
                100                 105
```

<210> SEQ ID NO 3
<211> LENGTH: 120
<212> TYPE: PRT
<213> ORGANISM: Artificial
<220> FEATURE:
<223> OTHER INFORMATION: single chain antibody

<400> SEQUENCE: 3

```
Ser Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Asn Ile Lys Asp
                20                  25                  30

Thr Tyr Ile His Trp Val Arg Gln Ala Pro Gly Lys Gly Leu Glu Trp
            35                  40                  45

Val Ala Arg Ile Tyr Pro Thr Asn Gly Tyr Thr Arg Tyr Ala Asp Ser
    50                  55                  60

Val Lys Gly Arg Phe Thr Ile Ser Ala Asp Thr Ser Lys Asn Thr Ala
65                  70                  75                  80

Tyr Leu Gln Met Asn Ser Leu Arg Ala Glu Asp Thr Ala Val Tyr Tyr
                85                  90                  95

Cys Ser Arg Trp Gly Asp Gly Phe Tyr Ala Met Asp Tyr Trp Gly
                100                 105                 110

Gln Gly Thr Leu Val Thr Val Ser
        115                 120
```

<210> SEQ ID NO 4
<211> LENGTH: 20
<212> TYPE: PRT
<213> ORGANISM: Artificial
<220> FEATURE:
<223> OTHER INFORMATION: single chain antibody

<400> SEQUENCE: 4

```
Lys Ser Asp Met Pro Met Ala Asp Pro Asn Arg Phe Arg Gly Lys Asn
1               5                   10                  15

Leu Val Phe His
        20
```

<210> SEQ ID NO 5
<211> LENGTH: 11
<212> TYPE: PRT
<213> ORGANISM: Artificial
<220> FEATURE:
<223> OTHER INFORMATION: single chain antibody

<400> SEQUENCE: 5

```
Ser Ser Gly Gly Gly Ser Gly Ser Gly Gly Ser
1               5                   10
```

<210> SEQ ID NO 6
<211> LENGTH: 2
<212> TYPE: PRT

-continued

<213> ORGANISM: Artificial
<220> FEATURE:
<223> OTHER INFORMATION: single chain antibody

<400> SEQUENCE: 6

Glu Asn
1

<210> SEQ ID NO 7
<211> LENGTH: 8
<212> TYPE: PRT
<213> ORGANISM: Artificial
<220> FEATURE:
<223> OTHER INFORMATION: HSV gD and single chain antibody

<400> SEQUENCE: 7

His Ser Ser Gly Gly Gly Ser Gly
1               5

<210> SEQ ID NO 8
<211> LENGTH: 12
<212> TYPE: PRT
<213> ORGANISM: Artificial
<220> FEATURE:
<223> OTHER INFORMATION: HSV gD and single chain antibody

<400> SEQUENCE: 8

Ser Ser Gly Gly Gly Ser Gly Ser Gly Gly Ser Gly
1               5                   10

<210> SEQ ID NO 9
<211> LENGTH: 596
<212> TYPE: PRT
<213> ORGANISM: Artificial
<220> FEATURE:
<223> OTHER INFORMATION: HSV gD and single chain antibody

<400> SEQUENCE: 9

Lys Tyr Ala Leu Ala Glu Asn Ser Asp Ile Gln Met Thr Gln Ser Pro
1               5                   10                  15

Ser Ser Leu Ser Ala Ser Val Gly Asp Arg Val Thr Ile Thr Cys Arg
            20                  25                  30

Ala Ser Gln Asp Val Asn Thr Ala Val Ala Trp Tyr Gln Gln Lys Pro
        35                  40                  45

Gly Lys Ala Pro Lys Leu Leu Ile Tyr Ser Ala Ser Phe Leu Tyr Ser
    50                  55                  60

Gly Val Pro Ser Arg Phe Ser Gly Ser Arg Ser Gly Thr Asp Phe Thr
65                  70                  75                  80

Leu Thr Ile Ser Ser Leu Gln Pro Glu Asp Phe Ala Thr Tyr Tyr Cys
                85                  90                  95

Gln Gln His Tyr Thr Thr Pro Pro Thr Phe Gly Gln Gly Thr Lys Val
            100                 105                 110

Glu Ile Lys Ser Asp Met Pro Met Ala Asp Pro Asn Arg Phe Arg Gly
        115                 120                 125

Lys Asn Leu Val Phe His Ser Glu Val Gln Leu Val Glu Ser Gly Gly
    130                 135                 140

Gly Leu Val Gln Pro Gly Gly Ser Leu Arg Leu Ser Cys Ala Ala Ser
145                 150                 155                 160

Gly Phe Asn Ile Lys Asp Thr Tyr Ile His Trp Val Arg Gln Ala Pro
                165                 170                 175

Gly Lys Gly Leu Glu Trp Val Ala Arg Ile Tyr Pro Thr Asn Gly Tyr

-continued

```
            180                 185                 190
Thr Arg Tyr Ala Asp Ser Val Lys Gly Arg Phe Thr Ile Ser Ala Asp
            195                 200                 205

Thr Ser Lys Asn Thr Ala Tyr Leu Gln Met Asn Ser Leu Arg Ala Glu
            210                 215                 220

Asp Thr Ala Val Tyr Tyr Cys Ser Arg Trp Gly Asp Gly Phe Tyr
225                 230                 235                 240

Ala Met Asp Tyr Trp Gly Gln Gly Thr Leu Val Thr Val Ser Ser
                245                 250                 255

Gly Gly Gly Ser Gly Ser Gly Gly Ser His Ile Gln Ala Gly Leu Pro
                260                 265                 270

Asp Pro Phe Gln Pro Ser Leu Pro Ile Thr Val Tyr Tyr Ala Val
            275                 280                 285

Leu Glu Arg Ala Cys Arg Ser Val Leu Leu Asn Ala Pro Ser Glu Ala
            290                 295                 300

Pro Gln Ile Val Arg Gly Ala Ser Glu Asp Val Arg Lys Gln Pro Tyr
305                 310                 315                 320

Asn Leu Thr Ile Ala Trp Phe Arg Met Gly Gly Asn Cys Ala Ile Pro
                325                 330                 335

Ile Thr Val Met Glu Tyr Thr Glu Cys Ser Tyr Asn Lys Ser Leu Gly
                340                 345                 350

Ala Cys Pro Ile Arg Thr Gln Pro Arg Trp Asn Tyr Tyr Asp Ser Phe
            355                 360                 365

Ser Ala Val Ser Glu Asp Asn Leu Gly Phe Leu Met His Ala Pro Ala
            370                 375                 380

Phe Glu Thr Ala Gly Thr Tyr Leu Arg Leu Val Lys Ile Asn Asp Trp
385                 390                 395                 400

Thr Glu Ile Thr Gln Phe Ile Leu Glu His Arg Ala Lys Gly Ser Cys
                405                 410                 415

Lys Tyr Ala Leu Pro Leu Arg Ile Pro Pro Ser Ala Cys Leu Ser Pro
            420                 425                 430

Gln Ala Tyr Gln Gln Gly Val Thr Val Asp Ser Ile Gly Met Leu Pro
            435                 440                 445

Arg Phe Ile Pro Glu Asn Gln Arg Thr Val Ala Val Tyr Ser Leu Lys
            450                 455                 460

Ile Ala Gly Trp His Gly Pro Lys Ala Pro Tyr Thr Ser Thr Leu Leu
465                 470                 475                 480

Pro Pro Glu Leu Ser Glu Thr Pro Asn Ala Thr Gln Pro Glu Leu Ala
                485                 490                 495

Pro Glu Asp Pro Glu Asp Ser Ala Leu Leu Glu Asp Pro Val Gly Thr
            500                 505                 510

Val Ala Pro Gln Ile Pro Pro Asn Trp His Ile Pro Ser Ile Gln Asp
            515                 520                 525

Ala Ala Thr Pro Tyr His Pro Pro Ala Thr Pro Asn Asn Met Gly Leu
            530                 535                 540

Ile Ala Gly Ala Val Gly Gly Ser Leu Leu Ala Ala Leu Val Ile Cys
545                 550                 555                 560

Gly Ile Val Tyr Trp Met Arg Arg Arg Thr Gln Lys Ala Pro Lys Arg
                565                 570                 575

Ile Arg Leu Pro His Ile Arg Glu Asp Asp Gln Pro Ser Ser His Gln
            580                 585                 590

Pro Leu Phe Tyr
            595
```

```
<210> SEQ ID NO 10
<211> LENGTH: 478
<212> TYPE: PRT
<213> ORGANISM: Artificial
<220> FEATURE:
<223> OTHER INFORMATION: HSV gD and single chain antibody

<400> SEQUENCE: 10
```

| | | | | | | | | | | | | | | |
|---|---|---|---|---|---|---|---|---|---|---|---|---|---|---|
| Lys | Tyr | Ala | Leu | Ala | Asp | Ala | Ser | Leu | Lys | Met | Ala | Asp | Pro | Asn | Arg |
| 1 | | | | 5 | | | | | 10 | | | | | 15 |

| | | | | | | | | | | | | | | | |
|---|---|---|---|---|---|---|---|---|---|---|---|---|---|---|---|
| Phe | Arg | Gly | Lys | Asp | Leu | Pro | Val | Leu | Asp | Gln | Leu | Thr | Asp | Pro | Pro |
| | | | 20 | | | | | 25 | | | | | 30 | | |

| Gly | Val | Arg | Arg | Val | Tyr | His | Ile | Gln | Ala | Gly | Leu | Pro | Asp | Pro | Phe |
|---|---|---|---|---|---|---|---|---|---|---|---|---|---|---|---|
| | | | 35 | | | | | 40 | | | | | 45 | | |

| Gln | Pro | Pro | Ser | Leu | Pro | Ile | Thr | Val | Tyr | Tyr | Ala | His | Ser | Ser | Gly |
|---|---|---|---|---|---|---|---|---|---|---|---|---|---|---|---|
| | 50 | | | | | 55 | | | | | 60 | | | | |

| Gly | Gly | Ser | Gly | Ser | Asp | Ile | Gln | Met | Thr | Gln | Ser | Pro | Ser | Ser | Leu |
|---|---|---|---|---|---|---|---|---|---|---|---|---|---|---|---|
| 65 | | | | | 70 | | | | | 75 | | | | | 80 |

| Ser | Ala | Ser | Val | Gly | Asp | Arg | Val | Thr | Ile | Thr | Cys | Arg | Ala | Ser | Gln |
|---|---|---|---|---|---|---|---|---|---|---|---|---|---|---|---|
| | | | | 85 | | | | | 90 | | | | | 95 | |

| Asp | Val | Asn | Thr | Ala | Val | Ala | Trp | Tyr | Gln | Gln | Lys | Pro | Gly | Lys | Ala |
|---|---|---|---|---|---|---|---|---|---|---|---|---|---|---|---|
| | | | 100 | | | | | 105 | | | | | 110 | | |

| Pro | Lys | Leu | Leu | Ile | Tyr | Ser | Ala | Ser | Phe | Leu | Tyr | Ser | Gly | Val | Pro |
|---|---|---|---|---|---|---|---|---|---|---|---|---|---|---|---|
| | | | 115 | | | | | 120 | | | | | 125 | | |

| Ser | Arg | Phe | Ser | Gly | Ser | Arg | Ser | Gly | Thr | Asp | Phe | Thr | Leu | Thr | Ile |
|---|---|---|---|---|---|---|---|---|---|---|---|---|---|---|---|
| | 130 | | | | | 135 | | | | | 140 | | | | |

| Ser | Ser | Leu | Gln | Pro | Glu | Asp | Phe | Ala | Thr | Tyr | Tyr | Cys | Gln | Gln | His |
|---|---|---|---|---|---|---|---|---|---|---|---|---|---|---|---|
| 145 | | | | | 150 | | | | | 155 | | | | | 160 |

| Tyr | Thr | Thr | Pro | Pro | Thr | Phe | Gly | Gln | Gly | Thr | Lys | Val | Glu | Ile | Lys |
|---|---|---|---|---|---|---|---|---|---|---|---|---|---|---|---|
| | | | | 165 | | | | | 170 | | | | | 175 | |

| Ser | Asp | Met | Pro | Met | Ala | Asp | Pro | Asn | Arg | Phe | Arg | Gly | Lys | Asn | Leu |
|---|---|---|---|---|---|---|---|---|---|---|---|---|---|---|---|
| | | | 180 | | | | | 185 | | | | | 190 | | |

| Val | Phe | His | Ser | Glu | Val | Gln | Leu | Val | Glu | Ser | Gly | Gly | Gly | Leu | Val |
|---|---|---|---|---|---|---|---|---|---|---|---|---|---|---|---|
| | | 195 | | | | | 200 | | | | | 205 | | | |

| Gln | Pro | Gly | Gly | Ser | Leu | Arg | Leu | Ser | Cys | Ala | Ala | Ser | Gly | Phe | Asn |
|---|---|---|---|---|---|---|---|---|---|---|---|---|---|---|---|
| | 210 | | | | | 215 | | | | | 220 | | | | |

| Ile | Lys | Asp | Thr | Tyr | Ile | His | Trp | Val | Arg | Gln | Ala | Pro | Gly | Lys | Gly |
|---|---|---|---|---|---|---|---|---|---|---|---|---|---|---|---|
| 225 | | | | | 230 | | | | | 235 | | | | | 240 |

| Leu | Glu | Trp | Val | Ala | Arg | Ile | Tyr | Pro | Thr | Asn | Gly | Tyr | Thr | Arg | Tyr |
|---|---|---|---|---|---|---|---|---|---|---|---|---|---|---|---|
| | | | | 245 | | | | | 250 | | | | | 255 | |

| Ala | Asp | Ser | Val | Lys | Gly | Arg | Phe | Thr | Ile | Ser | Ala | Asp | Thr | Ser | Lys |
|---|---|---|---|---|---|---|---|---|---|---|---|---|---|---|---|
| | | | 260 | | | | | 265 | | | | | 270 | | |

| Asn | Thr | Ala | Tyr | Leu | Gln | Met | Asn | Ser | Leu | Arg | Ala | Glu | Asp | Thr | Ala |
|---|---|---|---|---|---|---|---|---|---|---|---|---|---|---|---|
| | | 275 | | | | | 280 | | | | | 285 | | | |

| Val | Tyr | Tyr | Cys | Ser | Arg | Trp | Gly | Gly | Asp | Gly | Phe | Tyr | Ala | Met | Asp |
|---|---|---|---|---|---|---|---|---|---|---|---|---|---|---|---|
| | 290 | | | | | 295 | | | | | 300 | | | | |

| Tyr | Trp | Gly | Gln | Gly | Thr | Leu | Val | Thr | Val | Ser | Ser | Gly | Gly | Gly | Gly |
|---|---|---|---|---|---|---|---|---|---|---|---|---|---|---|---|
| 305 | | | | | 310 | | | | | 315 | | | | | 320 |

| Ser | Gly | Ser | Gly | Gly | Ser | Gly | Met | Leu | Pro | Arg | Phe | Ile | Pro | Glu | Asn |
|---|---|---|---|---|---|---|---|---|---|---|---|---|---|---|---|
| | | | | 325 | | | | | 330 | | | | | 335 | |

| Gln | Arg | Thr | Val | Ala | Val | Tyr | Ser | Leu | Lys | Ile | Ala | Gly | Trp | His | Gly |
|---|---|---|---|---|---|---|---|---|---|---|---|---|---|---|---|
| | | | 340 | | | | | 345 | | | | | 350 | | |

| Pro | Lys | Ala | Pro | Tyr | Thr | Ser | Thr | Leu | Leu | Pro | Pro | Glu | Leu | Ser | Glu |
|---|---|---|---|---|---|---|---|---|---|---|---|---|---|---|---|
| | | | 355 | | | | | 360 | | | | | 365 | | |

Thr Pro Asn Ala Thr Gln Pro Glu Leu Ala Pro Glu Asp Pro Glu Asp
    370                 375                 380

Ser Ala Leu Leu Glu Asp Pro Val Gly Thr Val Ala Pro Gln Ile Pro
385                 390                 395                 400

Pro Asn Trp His Ile Pro Ser Ile Gln Asp Ala Ala Thr Pro Tyr His
            405                 410                 415

Pro Pro Ala Thr Pro Asn Asn Met Gly Leu Ile Ala Gly Ala Val Gly
            420                 425                 430

Gly Ser Leu Leu Ala Ala Leu Val Ile Cys Gly Ile Val Tyr Trp Met
        435                 440                 445

Arg Arg Arg Thr Gln Lys Ala Pro Lys Arg Ile Arg Leu Pro His Ile
        450                 455                 460

Arg Glu Asp Asp Gln Pro Ser Ser His Gln Pro Leu Phe Tyr
465                 470                 475

<210> SEQ ID NO 11
<211> LENGTH: 82
<212> TYPE: DNA
<213> ORGANISM: Artificial
<220> FEATURE:
<223> OTHER INFORMATION: Synthetic primer

<400> SEQUENCE: 11
tgttcggtca taagcttcag cgcgaacgac caactacccc gatcatcagt tatccttaag    60
ccagtgaatt cgagctcggt ac                                             82

<210> SEQ ID NO 12
<211> LENGTH: 82
<212> TYPE: DNA
<213> ORGANISM: Artificial
<220> FEATURE:
<223> OTHER INFORMATION: Synthetic primer

<400> SEQUENCE: 12
acttatcgac tgtccacctt tcccccttc cagactcgct ttatatggag ttaaggtccc     60
gaccatgatt acgccaagct cc                                             82

<210> SEQ ID NO 13
<211> LENGTH: 35
<212> TYPE: DNA
<213> ORGANISM: Artificial
<220> FEATURE:
<223> OTHER INFORMATION: Synthetic primer

<400> SEQUENCE: 13
caacccggga tccaccggtc gccaccatgg tgagc                               35

<210> SEQ ID NO 14
<211> LENGTH: 38
<212> TYPE: DNA
<213> ORGANISM: Artificial
<220> FEATURE:
<223> OTHER INFORMATION: Synthetic primer

<400> SEQUENCE: 14
ccccttggga tcctgcccca ccccaccccc cagaatag                            38

<210> SEQ ID NO 15
<211> LENGTH: 41
<212> TYPE: DNA
<213> ORGANISM: Artificial

<220> FEATURE:
<223> OTHER INFORMATION: Synthetic primer

<400> SEQUENCE: 15
ttgccagtcg acattccgga tgagcattca tcaggcgggc a         41

<210> SEQ ID NO 16
<211> LENGTH: 39
<212> TYPE: DNA
<213> ORGANISM: Artificial
<220> FEATURE:
<223> OTHER INFORMATION: Synthetic primer

<400> SEQUENCE: 16
gcaaaaactc gagtgtagac ttccgttgaa ctgatggac         39

<210> SEQ ID NO 17
<211> LENGTH: 41
<212> TYPE: DNA
<213> ORGANISM: Artificial
<220> FEATURE:
<223> OTHER INFORMATION: Synthetic primer

<400> SEQUENCE: 17
ggaagtcaat tggaaggttt tgcgctgga tgtggctgcc c         41

<210> SEQ ID NO 18
<211> LENGTH: 41
<212> TYPE: DNA
<213> ORGANISM: Artificial
<220> FEATURE:
<223> OTHER INFORMATION: Synthetic primer

<400> SEQUENCE: 18
cacactgaat tcgcaatttg tcacaacacc ttctctagaa c         41

<210> SEQ ID NO 19
<211> LENGTH: 47
<212> TYPE: DNA
<213> ORGANISM: Artificial
<220> FEATURE:
<223> OTHER INFORMATION: Synthetic primer

<400> SEQUENCE: 19
tcctccgggg agccggcgcg tgtaccacat ccaggcaggc ctaccgg         47

<210> SEQ ID NO 20
<211> LENGTH: 54
<212> TYPE: DNA
<213> ORGANISM: Artificial
<220> FEATURE:
<223> OTHER INFORMATION: Synthetic primer

<400> SEQUENCE: 20 aggggtgac ggtgggctcg atcgggatgc tgcccaacat catccccgag aacc         54

<210> SEQ ID NO 21
<211> LENGTH: 33
<212> TYPE: DNA
<213> ORGANISM: Artificial
<220> FEATURE:
<223> OTHER INFORMATION: single chain antibody

<400> SEQUENCE: 21
tcgagtggcg gtggctctgg ttccggtgga tcc         33

<210> SEQ ID NO 22
<211> LENGTH: 38
<212> TYPE: DNA
<213> ORGANISM: Artificial
<220> FEATURE:
<223> OTHER INFORMATION: Synthetic primer

<400> SEQUENCE: 22
caaatatgcc ttggcggaga attctctcaa gatggccg                              38

<210> SEQ ID NO 23
<211> LENGTH: 34
<212> TYPE: DNA
<213> ORGANISM: Artificial
<220> FEATURE:
<223> OTHER INFORMATION: Synthetic primer

<400> SEQUENCE: 23
cgggggtccg gcgcggatcc cacatccagg cggg                                  34

<210> SEQ ID NO 24
<211> LENGTH: 37
<212> TYPE: DNA
<213> ORGANISM: Artificial
<220> FEATURE:
<223> OTHER INFORMATION: Synthetic primer

<400> SEQUENCE: 24
gcaaaggaat tccgatatcc agatgaccca gtccccg                               37

<210> SEQ ID NO 25
<211> LENGTH: 39
<212> TYPE: DNA
<213> ORGANISM: Artificial
<220> FEATURE:
<223> OTHER INFORMATION: Synthetic primer

<400> SEQUENCE: 25
cggaggatcc accggaacca gagccaccgc cactcgagg                             39

<210> SEQ ID NO 26
<211> LENGTH: 24
<212> TYPE: DNA
<213> ORGANISM: Artificial
<220> FEATURE:
<223> OTHER INFORMATION: single chain antibody

<400> SEQUENCE: 26
catagtagtg gcggtggctc tgga                                             24

<210> SEQ ID NO 27
<211> LENGTH: 36
<212> TYPE: DNA
<213> ORGANISM: Artificial
<220> FEATURE:
<223> OTHER INFORMATION: single chain antibody

<400> SEQUENCE: 27
tcgagtggcg gtggctctgg ttccggtgga tccggt                                36

<210> SEQ ID NO 28
<211> LENGTH: 34
<212> TYPE: DNA
<213> ORGANISM: Artificial
<220> FEATURE:
<223> OTHER INFORMATION: Synthetic primer -continued

```
<400> SEQUENCE: 28
acggtttact acgcccatat ggagcgcgcc tgcc                                34

<210> SEQ ID NO 29
<211> LENGTH: 34
<212> TYPE: DNA
<213> ORGANISM: Artificial
<220> FEATURE:
<223> OTHER INFORMATION: Synthetic primer

<400> SEQUENCE: 29
gacggtggac agcatccata tgctgccccg cttc                                34

<210> SEQ ID NO 30
<211> LENGTH: 27
<212> TYPE: DNA
<213> ORGANISM: Artificial
<220> FEATURE:
<223> OTHER INFORMATION: Oligo

<400> SEQUENCE: 30
tagtagtggc ggtggctctg gatccgg                                        27

<210> SEQ ID NO 31
<211> LENGTH: 27
<212> TYPE: DNA
<213> ORGANISM: Artificial
<220> FEATURE:
<223> OTHER INFORMATION: Oligo

<400> SEQUENCE: 31
taccggatcc agagccaccg ccactac                                        27

<210> SEQ ID NO 32
<211> LENGTH: 36
<212> TYPE: DNA
<213> ORGANISM: Artificial
<220> FEATURE:
<223> OTHER INFORMATION: Synthetic primer

<400> SEQUENCE: 32
ggcttatgga tccgatatcc agatgaccca gtcccc                              36

<210> SEQ ID NO 33
<211> LENGTH: 39
<212> TYPE: DNA
<213> ORGANISM: Artificial
<220> FEATURE:
<223> OTHER INFORMATION: Synthetic primer

<400> SEQUENCE: 33
cggaggatcc accggaacca gagccaccgc cactcgagg                           39

<210> SEQ ID NO 34
<211> LENGTH: 394
<212> TYPE: PRT
<213> ORGANISM: herpes simplex virus

<400> SEQUENCE: 34

Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
            20                  25                  30
```

```
Ser Leu Lys Met Ala Asp Pro Asn Arg Phe Arg Gly Lys Asp Leu Pro
         35                  40                  45

Val Leu Asp Gln Leu Thr Asp Pro Pro Gly Val Arg Arg Val Tyr His
 50                  55                  60

Ile Gln Ala Gly Leu Pro Asp Pro Phe Gln Pro Pro Ser Leu Pro Ile
 65                  70                  75                  80

Thr Val Tyr Tyr Ala Val Leu Glu Arg Ala Cys Arg Ser Val Leu Leu
                 85                  90                  95

Asn Ala Pro Ser Glu Ala Pro Gln Ile Val Arg Gly Ala Ser Glu Asp
                100                 105                 110

Val Arg Lys Gln Pro Tyr Asn Leu Thr Ile Ala Trp Phe Arg Met Gly
        115                 120                 125

Gly Asn Cys Ala Ile Pro Ile Thr Val Met Glu Tyr Thr Glu Cys Ser
    130                 135                 140

Tyr Asn Lys Ser Leu Gly Ala Cys Pro Ile Arg Thr Gln Pro Arg Trp
145                 150                 155                 160

Asn Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
            180                 185                 190

Val Lys Ile Asn Asp Trp Thr Glu Ile Thr Gln Phe Ile Leu Glu His
        195                 200                 205

Arg Ala Lys Gly Ser Cys Lys Tyr Ala Leu Pro Leu Arg Ile Pro Pro
    210                 215                 220

Ser Ala Cys Leu Ser Pro Gln Ala Tyr Gln Gln Gly Val Thr Val Asp
225                 230                 235                 240

Ser Ile Gly Met Leu Pro Arg Phe Ile Pro Glu Asn Gln Arg Thr Val
                245                 250                 255

Ala Val Tyr Ser Leu Lys Ile Ala Gly Trp His Gly Pro Lys Ala Pro
            260                 265                 270

Tyr Thr Ser Thr Leu Leu Pro Pro Glu Leu Ser Glu Thr Pro Asn Ala
        275                 280                 285

Thr Gln Pro Glu Leu Ala Pro Glu Asp Pro Glu Asp Ser Ala Leu Leu
    290                 295                 300

Glu Asp Pro Val Gly Thr Val Ala Pro Gln Ile Pro Pro Asn Trp His
305                 310                 315                 320

Ile Pro Ser Ile Gln Asp Ala Ala Thr Pro Tyr His Pro Pro Ala Thr
                325                 330                 335

Pro Asn Asn Met Gly Leu Ile Ala Gly Ala Val Gly Gly Ser Leu Leu
            340                 345                 350

Ala Ala Leu Val Ile Cys Gly Ile Val Tyr Trp Met Arg Arg Arg Thr
        355                 360                 365

Gln Lys Ala Pro Lys Arg Ile Arg Leu Pro His Ile Arg Glu Asp Asp
    370                 375                 380

Gln Pro Ser Ser His Gln Pro Leu Phe Tyr
385                 390
```

<210> SEQ ID NO 35
<211> LENGTH: 1185
<212> TYPE: DNA
<213> ORGANISM: herpes simplex virus

<400> SEQUENCE: 35 atggggggggg ctgccgccag gttgggggcc gtgattttgt ttgtcgtcat agtgggcctc     60

-continued

| | |
|---|---|
| catggggtcc gcggcaaata tgccttggcg gatgcctctc tcaagatggc cgaccccaat | 120 |
| cgctttcgcg gcaaagacct tccggtcctg gaccagctga ccgaccctcc ggggtccgg | 180 |
| cgcgtgtacc acatccaggc gggcctacca gacccgttcc agccccccag cctcccgatc | 240 |
| acggtttact acgccgtgtt ggagcgcgcc tgccgcagcg tgctcctaaa cgcaccgtcg | 300 |
| gaggccccc agattgtccg cggggcctcc gaagacgtcc ggaaacaacc ctacaacctg | 360 |
| accatcgctt ggtttcggat gggaggcaac tgtgctatcc ccatcacggt catggagtac | 420 |
| accgaatgct cctacaacaa gtctctgggg gcctgtccca tccgaacgca gccccgctgg | 480 |
| aactactatg acagcttcag cgccgtcagc gaggataacc tggggttcct gatgcacgcc | 540 |
| cccgcgtttg agaccgccgg cacgtacctg cggctcgtga agataaacga ctggacggag | 600 |
| attacacagt ttatcctgga gcaccgagcc aagggctcct gtaagtacgc cctcccgctg | 660 |
| cgcatccccc cgtcagcctg cctgtccccc caggcctacc agcaggggt gacggtggac | 720 |
| agcatcggga tgctgccccg cttcatcccc gagaaccagc gcaccgtcgc cgtatacagc | 780 |
| ttgaagatcg ccgggtggca cgggcccaag gccccataca cgagcaccct gctgcccccg | 840 |
| gagctgtccg agaccccaa cgccacgcag ccagaactcg ccccggaaga ccccgaggat | 900 |
| tcggccctct tggaggaccc cgtggggacg gtggcgccgc aaatcccacc aaactggcac | 960 |
| ataccgtcga tccaggacgc cgcgacgcct accatccccc ggccaccccc gaacaacatg | 1020 |
| ggcctgatcg ccggcgcggt gggcggcagt ctcctggcag ccctggtcat ttgcggaatt | 1080 |
| gtgtactgga tgcgccgccg cactcaaaaa gccccaaagc gcatacgcct cccccacatc | 1140 |
| cgggaagacg accagccgtc ctcgcaccag cccttgtttt actag | 1185 |

<210> SEQ ID NO 36
<211> LENGTH: 1512
<212> TYPE: DNA
<213> ORGANISM: Artificial
<220> FEATURE:
<223> OTHER INFORMATION: HSV gD and single chain antibody

<400> SEQUENCE: 36

| | |
|---|---|
| atggggggg ctgccgccag gttgggggcc gtgattttgt ttgtcgtcat agtgggcctc | 60 |
| catggggtcc gcggcaaata tgccttggcg gatgcctctc tcaagatggc cgaccccaat | 120 |
| cgctttcgcg gcaaagacct tccggtcctg gaccagctga ccgaccctcc ggggtccgg | 180 |
| cgcgtgtacc acatccaggc gggcctacca gacccgttcc agccccccag cctcccgatc | 240 |
| acggtttact acgcccatag tagtggcggt ggctctggat ccgatatcca gatgacccag | 300 |
| tccccgagct ccctgtccgc ctctgtgggc gatagggtca ccatcacctg ccgtgccagt | 360 |
| caggatgtga atactgctgt agcctggtat aacagaaac caggaaaagc tccgaagctt | 420 |
| ctgatttact cggcatcctt cctctactct ggagtcccct tcgcttctc tggtagccgt | 480 |
| tccgggacgg atttcactct gaccatcagc agtctgcagc cggaagactt cgcaacttat | 540 |
| tactgtcagc aacattatac tactcctccc acgttcggac agggtaccaa ggtggagatc | 600 |
| aaatcggata tgccgatggc tgatccgaac cgtttccgcg gtaagaacct ggttttcat | 660 |
| tctgaggttc agctggtgga gtctggcggt ggcctggtgc agccaggggg ctcactccgt | 720 |
| ttgtcctgtg cagcttctgg cttcaacatt aaagacacct atatacactg ggtgcgtcag | 780 |
| gccccgggta agggcctgga atgggttgca aggattatc ctacgaatgg ttatactaga | 840 |
| tatgccgata gcgtcaaggg ccgttttcact ataagcgcag acacatccaa aaacacagcc | 900 |
| tacctacaaa tgaacagctt aagagctgag gacactgccg tctattattg tagccgctgg | 960 |

```
ggaggggacg gcttctatgc tatggactac tggggtcaag gaacactagt caccgtctcc    1020
tcgagtggcg gtggctctgg ttccggtgga tccggtatgc tgccccgctt catccccgag    1080
aaccagcgca ccgtcgccgt atacagcttg aagatcgccg ggtggcacgg gcccaaggcc    1140
ccatacacga gcaccctgct gccccggag ctgtccgaga cccccaacgc cacgcagcca    1200
gaactcgccc cggaagaccc cgaggattcg gccctcttgg aggacccgt ggggacggtg    1260 gcgccgcaaa tcccaccaaa ctggcacata ccgtcgatcc aggacgccgc gacgccttac    1320
catcccccgg ccaccccgaa caacatgggc ctgatcgccg gcgcggtggg cggcagtctc    1380
ctggcagccc tggtcatttg cggaattgtg tactggatgc gcgccgcac tcaaaaagcc    1440 ccaaagcgca tacgcctccc ccacatccgg gaagacgacc agccgtcctc gcaccagccc    1500
ttgttttact ag                                                       1512

<210> SEQ ID NO 37
<211> LENGTH: 1866
<212> TYPE: DNA
<213> ORGANISM: Artificial
<220> FEATURE:
<223> OTHER INFORMATION: HSV gD and single chain antibody

<400> SEQUENCE: 37 atggggggg ctgccgccag gttgggggcc gtgattttgt ttgtcgtcat agtgggcctc      60
catggggtcc gcggcaaata tgccttggcg gagaattccg atatccagat gacccagtcc    120
ccgagctccc tgtccgcctc tgtgggcgat agggtcacca tcacctgccg tgccagtcag    180
gatgtgaata tgctgtagc ctggtatcaa cagaaaccag aaaagctcc gaagcttctg     240 atttactcgg catccttcct ctactctgga gtcccttctc gcttctctgg tagccgttcc    300
gggacggatt tcactctgac catcagcagt ctgcagccgg aagacttcgc aacttattac    360
tgtcagcaac attatactac tcctcccacg ttcggacagg gtaccaaggt ggagatcaaa    420
tcggatatgc cgatggctga tccgaaccgt ttccgcggta agaacctggt ttttcattct    480
gaggttcagc tggtggagtc tggcggtggc ctggtcagc caggggggctc actccgtttg    540 tcctgtgcag cttctggctt caacattaaa gacacctata tacactgggt gcgtcaggcc    600
ccgggtaagg gcctggaatg ggttgcaagg atttatccta cgaatggtta tactagatat    660
gccgatagcg tcaagggccg tttcactata agcgcagaca catccaaaaa cacagcctac    720
ctacaaatga acagcttaag agctgaggac actgccgtct attattgtag ccgctgggga    780
ggggacgcct tctatgctat ggactactgg ggtcaaggaa cactagtcac cgtctcctcg    840
agtggcggtg gctctggttc cggtggatcc cacatccagg cgggcctacc agacccgttc    900 cagccccca gcctccgat cacggtttac tacgccgtgt ggagcgcgc ctgccgcagc    960 gtgctcctaa cgcaccgtc ggaggccccc cagattgtcc gcggggcctc gaagacgtc    1020 cggaaacaac cctacaacct gaccatcgct tggtttcgga tgggaggcaa ctgtgctatc    1080
cccatcacgg tcatggagta caccgaatgc tcctacaaca agtctctggg ggcctgtccc    1140
atccgaacgc agccccgctg gaactactat gacagcttca gcgccgtcag cgaggataac    1200 ctgggttcc tgatgcacgc cccgcgttt gagaccgccg gcacgtacct gcggctcgtg    1260
aagataaacg actggacgga gattacacag tttatcctgg agcaccgagc caagggctcc    1320
tgtaagtacg ccctcccgct gcgcatcccc ccgtcagcct gcctgtcccc ccaggcctac    1380
cagcaggggg tgacggtgga cagcatcggg atgctgcccc gcttcatccc cgagaaccag    1440
```

-continued

```
cgcaccgtcg ccgtatacag cttgaagatc gccgggtggc acgggcccaa ggccccatac      1500
acgagcaccc tgctgccccc ggagctgtcc gagaccccca acgccacgca gccagaactc      1560
gccccggaag accccgagga ttcggccctc ttggaggacc ccgtggggac ggtggcgccg      1620
caaatcccac caaactggca cataccgtcg atccaggacg ccgcgacgcc ttaccatccc      1680
ccggccaccc cgaacaacat gggcctgatc gccggcgcgg tgggcggcag tctcctggca      1740
gccctggtca tttgcggaat tgtgtactgg atgcgccgcc gcactcaaaa agccccaaag      1800
cgcatacgcc tccccacat ccgggaagac gaccagccgt cctcgcacca gcccttgttt       1860
tactag                                                                 1866
```

<210> SEQ ID NO 38
<211> LENGTH: 625
<212> TYPE: PRT
<213> ORGANISM: Artificial
<220> FEATURE:
<223> OTHER INFORMATION: HSV gD and single chain antibody

<400> SEQUENCE: 38

```
Lys Tyr Ala Leu Ala Asp Ala Ser Leu Lys Met Ala Asp Pro Asn Arg
1               5                   10                  15

Phe Arg Gly Lys Gly Ile Pro Val Ser Asp Ile Gln Met Thr Gln Ser
            20                  25                  30

Pro Ser Ser Leu Ser Ala Ser Val Gly Asp Arg Val Thr Ile Thr Cys
        35                  40                  45

Arg Ala Ser Gln Asp Val Asn Thr Ala Val Ala Trp Tyr Gln

```
Gly Ser Arg Arg Val Tyr His Ile Gln Ala Gly Leu Pro Asp Pro Phe
    290                 295                 300

Gln Pro Pro Ser Leu Pro Ile Thr Val Tyr Tyr Ala Val Leu Glu Arg
305                 310                 315                 320

Ala Cys Arg Ser Val Leu Leu Asn Ala Pro Ser Glu Ala Pro Gln Ile
                325                 330                 335

Val Arg Gly Ala Ser Glu Asp Val Arg Lys Gln Pro Tyr Asn Leu Thr
            340                 345                 350

Ile Ala Trp Phe Arg Met Gly Gly Asn Cys Ala Ile Pro Ile Thr Val
        355                 360                 365

Met Glu Tyr Thr Glu Cys Ser Tyr Asn Lys Ser Leu Gly Ala Cys Pro
    370                 375                 380

Ile Arg Thr Gln Pro Arg Trp Asn Tyr Tyr Asp Ser Phe Ser Ala Val
385                 390                 395                 400

Ser Glu Asp Asn Leu Gly Phe Leu Met His Ala Pro Ala Phe Glu Thr
                405                 410                 415

Ala Gly Thr Tyr Leu Arg Leu Val Lys Ile Asn Asp Trp Thr Glu Ile
            420                 425                 430

Thr Gln Phe Ile Leu Glu His Arg Ala Lys Gly Ser Cys Lys Tyr Ala
        435                 440                 445

Leu Pro Leu Arg Ile Pro Pro Ser Ala Cys Leu Ser Pro Gln Ala Tyr
    450                 455                 460

Gln Gln Gly Val Thr Val Asp Ser Ile Gly Met Leu Pro Arg Phe Ile
465                 470                 475                 480

Pro Glu Asn Gln Arg Thr Val Ala Val Tyr Ser Leu Lys Ile Ala Gly
                485                 490                 495

Trp His Gly Pro Lys Ala Pro Tyr Thr Ser Thr Leu Leu Pro Pro Glu
            500                 505                 510

Leu Ser Glu Thr Pro Asn Ala Thr Gln Pro Glu Leu Ala Pro Glu Asp
        515                 520                 525

Pro Glu Asp Ser Ala Leu Leu Glu Asp Pro Val Gly Thr Val Ala Pro
    530                 535                 540

Gln Ile Pro Pro Asn Trp His Ile Pro Ser Ile Gln Asp Ala Ala Thr
545                 550                 555                 560

Pro Tyr His Pro Pro Ala Thr Pro Asn Asn Met Gly Leu Ile Ala Gly
                565                 570                 575

Ala Val Gly Gly Ser Leu Leu Ala Ala Leu Val Ile Cys Gly Ile Val
            580                 585                 590

Tyr Trp Met Arg Arg Arg Thr Gln Lys Ala Pro Lys Arg Ile Arg Leu
        595                 600                 605

Pro His Ile Arg Glu Asp Asp Gln Pro Ser Ser His Gln Pro Leu Phe
    610                 615                 620

Tyr
625

<210> SEQ ID NO 39
<211> LENGTH: 1953
<212> TYPE: DNA
<213> ORGANISM: Artificial
<220> FEATURE:
<223> OTHER INFORMATION: HSV gD and single chain antibody

<400> SEQUENCE: 39 atgg

-continued

```
catgggtcc gcggcaaata tgccttggcg atgcctctc tcaagatggc cgaccccaat    120
cgctttcgcg gcaaaggaat tccggtctcc gatatccaga tgacccagtc cccgagctcc    180
ctgtccgcct ctgtgggcga tagggtcacc atcacctgcc gtgccagtca ggatgtgaat    240
actgctgtag cctggtatca acagaaacca ggaaaagctc cgaagcttct gatttactcg    300
gcatccttcc tctactctgg agtcccttct cgcttctctg gtagccgttc cgggacggat    360
ttcactctga ccatcagcag tctgcagccg aagacttcg caacttatta ctgtcagcaa    420
cattatacta ctcctcccac gttcggacag ggtaccaagg tggagatcaa atcggatatg    480
ccgatggctg atccgaaccg tttccgcggt aagaacctgg tttttcattc tgaggttcag    540
ctggtggagt ctggcggtgg cctggtgcag ccagggggct cactccgttt gtcctgtgca    600
gcttctggct tcaacattaa agacacctat atacactggg tgcgtcaggc cccgggtaag    660
ggcctggaat gggttgcaag gatttatcct acgaatggtt atactagata tgccgatagc    720
gtcaagggcc gtttcactat aagcgcagac acatccaaaa acacagccta cctacaaatg    780
aacagcttaa gagctgagga cactgccgtc tattattgta gccgctgggg aggggacggc    840
ttctatgcta tggactactg gggtcaagga acactagtca ccgtctcctc gagtggcggt    900
ggctctggtt ccggtctgga ccagctgacg atcctccgg ggagccggcg cgtgtaccac    960
atccaggcag gcctaccgga cccgttccag cccccagcc tcccgatcac ggtttactac   1020
gccgtgttgg agcgcgcctg ccgcagcgtg ctcctaaacg caccgtcgga ggccccccag   1080
attgtccgcg gggcctccga agacgtccgg aaacaaccct acaacctgac catcgcttgg   1140
tttcggatgg gaggcaactg tgctatcccc atcacggtca tggagtacac cgaatgctcc   1200
tacaacaagt ctctggggc ctgtcccatc cgaacgcagc cccgctggaa ctactatgac   1260
agcttcagcg ccgtcagcga ggataacctg gggttcctga tgcacgcccc cgcgtttgag   1320
accgccggca cgtacctgcg gctcgtgaag ataaacgact ggacggagat tacacagttt   1380
atcctggagc accagccaa gggctcctgt aagtacgccc tcccgctgcg catcccccg   1440
tcagcctgcc tgtccccca ggcctaccag caggggtga cggtggacag catcgggatg   1500
ctgccccgct tcatcccga gaaccagcgc accgtcgccg tatacagctt gaagatcgcc   1560
gggtggcacg ggcccaaggc cccatacacg agcaccctgc tgccccggga gctgtccgag   1620
acccccaacg ccacgcagcc agaactcgcc ccggaagacc ccgaggattc ggccctcttg   1680
gaggaccccg tggggacggt ggcgccgcaa atccaccaa actggcacat accgtcgatc   1740
caggacgccg cgacgcctta ccatcccccg gccaccccga caacatgggg cctgatcgcc   1800
ggcgcggtgg gcggcagtct cctggcagcc ctggtcattt gcggaattgt gtactggatg   1860
cgccgccgca ctcaaaaagc cccaaagcgc atacgcctcc cccacatccg gaagacgac   1920
cagccgtcct cgcaccagcc cttgttttac tag   1953
```

<210> SEQ ID NO 40
<211> LENGTH: 625
<212> TYPE: PRT
<213> ORGANISM: Artificial
<220> FEATURE:
<223> OTHER INFORMATION: HSV gD and single chain antibody

<400> SEQUENCE: 40

```
Lys Tyr Ala Leu Ala Asp Ala Ser Leu Lys Met Ala Asp Pro Asn Arg
  1               5                  10                  15

Phe Arg Gly Lys Gly Ile Pro Val Ser Asp Ile Gln Met Thr Gln Ser
             20                  25                  30
```

```
Pro Ser Ser Leu Ser Ala Ser Val Gly Asp Arg Val Thr Ile Thr Cys
        35                  40                  45

Arg Ala Ser Gln Asp Val Asn Thr Ala Val Ala Trp Tyr Gln Gln Lys
        50                  55                  60

Pro Gly Lys Ala Pro Lys Leu Leu Ile Tyr Ser Ala Ser Phe Leu Tyr
65                  70                  75                  80

Ser Gly Val Pro Ser Arg Phe Ser Gly Ser Arg Ser Gly Thr Asp Phe
                85                  90                  95

Thr Leu Thr Ile Ser Ser Leu Gln Pro Glu Asp Phe Ala Thr Tyr Tyr
                100                 105                 110

Cys Gln Gln His Tyr Thr Thr Pro Pro Thr Phe Gly Gln Gly Thr Lys
                115                 120                 125

Val Glu Ile Lys Ser Asp Met Pro Met Ala Asp Pro Asn Arg Phe Arg
        130                 135                 140

Gly Lys Asn Leu Val Phe His Ser Glu Val Gln Leu Val Glu Ser Gly
145                 150                 155                 160

Gly Gly Leu Val Gln Pro Gly Gly Ser Leu Arg Leu Ser Cys Ala Ala
                165                 170                 175

Ser Gly Phe Asn Ile Lys Asp Thr Tyr Ile His Trp Val Arg Gln Ala
                180                 185                 190

Pro Gly Lys Gly Leu Glu Trp Val Ala Arg Ile Tyr Pro Thr Asn Gly
                195                 200                 205

Tyr Thr Arg Tyr Ala Asp Ser Val Lys Gly Arg Phe Thr Ile Ser Ala
        210                 215                 220

Asp Thr Ser Lys Asn Thr Ala Tyr Leu Gln Met Asn Ser Leu Arg Ala
225                 230                 235                 240

Glu Asp Thr Ala Val Tyr Tyr Cys Ser Arg Trp Gly Gly Asp Gly Phe
                245                 250                 255

Tyr Ala Met Asp Tyr Trp Gly Gln Gly Thr Leu Val Thr Val Ser Ser
                260                 265                 270

Ser Gly Gly Gly Ser Gly Ser Gly Leu Asp Gln Leu Thr Asp Pro Pro
                275                 280                 285

Gly Ser Arg Arg Val Tyr His Ile Gln Ala Gly Leu Pro Asp Pro Phe
        290                 295                 300

Gln Pro Pro Ser Leu Pro Ile Thr Val Tyr Tyr Ala Val Leu Glu Arg
305                 310                 315                 320

Ala Cys Arg Ser Val Leu Leu Asn Ala Pro Ser Glu Ala Pro Gln Ile
                325                 330                 335

Val Arg Gly Ala Ser Glu Asp Val Arg Lys Gln Pro Tyr Asn Leu Thr
                340                 345                 350

Ile Ala Trp Phe Arg Met Gly Gly Asn Cys Ala Ile Pro Ile Thr Val
                355                 360                 365

Met Glu Tyr Thr Glu Cys Ser Tyr Asn Lys Ser Leu Gly Ala Cys Pro
        370                 375                 380

Ile Arg Thr Gln Pro Arg Trp Asn Tyr Tyr Asp Ser Phe Ser Ala Val
385                 390                 395                 400

Ser Glu Asp Asn Leu Gly Phe Leu Met His Ala Pro Ala Phe Glu Thr
                405                 410                 415

Ala Gly Thr Tyr Leu Arg Leu Val Lys Ile Asn Asp Trp Thr Glu Ile
                420                 425                 430

Thr Gln Phe Ile Leu Glu His Arg Ala Lys Gly Ser Cys Lys Tyr Ala
        435                 440                 445
```

-continued

```
Leu Pro Leu Arg Ile Pro Pro Ser Ala Cys Leu Ser Pro Gln Ala Tyr
    450                 455                 460

Gln Gln Gly Val Thr Val Gly Ser Ile Gly Met Leu Pro Asn Ile Ile
465                 470                 475                 480

Pro Glu Asn Gln Arg Thr Val Ala Val Tyr Ser Leu Lys Ile Ala Gly
                485                 490                 495

Trp His Gly Pro Lys Ala Pro Tyr Thr Ser Thr Leu Leu Pro Pro Glu
            500                 505                 510

Leu Ser Glu Thr Pro Asn Ala Thr Gln Pro Glu Leu Ala Pro Glu Asp
        515                 520                 525

Pro Glu Asp Ser Ala Leu Leu Glu Asp Pro Val Gly Thr Val Ala Pro
    530                 535                 540

Gln Ile Pro Pro Asn Trp His Ile Pro Ser Ile Gln Asp Ala Ala Thr
545                 550                 555                 560

Pro Tyr His Pro Pro Ala Thr Pro Asn Asn Met Gly Leu Ile Ala Gly
                565                 570                 575

Ala Val Gly Gly Ser Leu Leu Ala Ala Leu Val Ile Cys Gly Ile Val
            580                 585                 590

Tyr Trp Met Arg Arg Arg Thr Gln Lys Ala Pro Lys Arg Ile Arg Leu
        595                 600                 605

Pro His Ile Arg Glu Asp Asp Gln Pro Ser Ser His Gln Pro Leu Phe
    610                 615                 620

Tyr
625
```

<210> SEQ ID NO 41
<211> LENGTH: 1953
<212> TYPE: DNA
<213> ORGANISM: Artificial
<220> FEATURE:
<223> OTHER INFORMATION: HSV gD and single chain antibody

<400> SEQUENCE: 41

```
atgggggggg ctgccgccag gttgggggcc gtgattttgt ttgtcgtcat agtgggcctc      60
catggggtcc gcggcaaata tgccttggcg gatgcctctc tcaagatggc cgaccccaat     120
cgctttcgcg gcaaaggaat tccggtctcc gatatccaga tgacccagtc cccgagctcc     180
ctgtccgcct ctgtgggcga tagggtcacc atcacctgcc gtgccagtca ggatgtgaat     240
actgctgtag cctggtatca acagaaacca ggaaaagctc cgaagcttct gatttactcg     300
gcatccttcc tctactctgg agtcccttct cgcttctctg gtagccgttc cgggacggat     360
ttcactctga ccatcagcag tctgcagccg gaagacttcg caacttatta ctgtcagcaa     420
cattatacta ctcctcccac gttcggacag ggtaccaagg tggagatcaa atcggatatg     480
ccgatggctg atccgaaccg tttccgcggt aagaacctgg tttttcattc tgaggttcag     540
ctggtggagt ctggcggtgg cctggtgcag ccagggggct cactccgttt gtcctgtgca     600
gcttctggct tcaacattaa agacacctat atacactggg tgcgtcaggc cccgggtaag     660
ggcctggaat gggttgcaag gatttatcct acgaatggtt atactagata tgccgatagc     720
gtcaagggcc gtttcactat aagcgcagac acatccaaaa acacagccta cctacaaatg     780
aacagcttaa gagctgagga cactgccgtc tattattgta gccgctgggg aggggacggc     840
ttctatgcta tggactactg gggtcaagga acactagtca ccgtctcctc gagtggcggt     900
ggctctggtt ccggtctgga ccagctgacg gatcctccgg ggagccggcg cgtgtaccac     960
atccaggcag gcctaccgga cccgttccag cccccccagcc tcccgatcac ggtttactac    1020
```

```
gccgtgttgg agcgcgcctg ccgcagcgtg ctcctaaacg caccgtcgga ggcccccag    1080 attgtccgcg gggcctccga agacgtccgg aaacaaccct acaacctgac catcgcttgg    1140
tttcggatgg gaggcaactg tgctatcccc atcacggtca tggagtacac cgaatgctcc    1200
tacaacaagt ctctgggggc ctgtcccatc cgaacgcagc cccgctggaa ctactatgac    1260
agcttcagcg ccgtcagcga ggataacctg gggttcctga tgcacgcccc cgcgtttgag    1320
accgccggca cgtacctgcg gctcgtgaag ataaacgact ggacggagat tacacagttt    1380
atcctggagc accgagccaa gggctcctgt aagtacgccc tcccgctgcg catcccccg    1440 tcagcctgcc tgtcccccca ggcctaccag caggggtga cggtgggctc gatcgggatg    1500
ctgcccaaca tcatccccga gaaccagcgc accgtcgccg tatacagctt gaagatcgcc    1560
gggtggcacg ggcccaaggc ccatacacg agcaccctgc tgcccccgga gctgtccgag    1620 accccccaacg ccacgcagcc agaactcgcc ccggaagacc ccgaggattc ggccctcttg    1680
gaggaccccg tggggacggt ggcgccgcaa atcccaccaa actggcacat accgtcgatc    1740
caggacgccg cgacgcctta ccatccccg gccaccccga caacatggg cctgatcgcc    1800 ggcgcggtgg gcggcagtct cctggcagcc ctggtcattt gcggaattgt gtactggatg    1860
cgccgccgca ctcaaaaagc cccaaagcgc atacgcctcc ccacatccg ggaagacgac    1920 cagccgtcct cgcaccagcc cttgttttac tag                                1953
```

<210> SEQ ID NO 42
<211> LENGTH: 625
<212> TYPE: PRT
<213> ORGANISM: Artificial
<220> FEATURE:
<223> OTHER INFORMATION: HSV gD and single chain antibody

<400> SEQUENCE: 42

```
Lys Tyr Ala Leu Ala Asp Ala Ser Leu Lys Met Ala Asp Pro Asn Arg
1               5                   10                  15

Phe Arg Gly Lys Gly Ile Pro Val Ser Asp Ile Gln Met Thr Gln Ser
            20                  25                  30

Pro Ser Ser Leu Ser Ala Ser Val Gly Asp Arg Val Thr Ile Thr Cys
        35                  40                  45

Arg Ala Ser Gln Asp Val Asn Thr Ala Val Ala Trp Tyr Gln Gln Lys
    50                  55                  60

Pro Gly Lys Ala Pro Lys Leu Leu Ile Tyr Ser Ala Ser Phe Leu Tyr
65                  70                  75                  80

Ser Gly Val Pro Ser Arg Phe Ser Gly Ser Arg Ser Gly Thr Asp Phe
                85                  90                  95

Thr Leu Thr Ile Ser Ser Leu Gln Pro Glu Asp Phe Ala Thr Tyr Tyr
            100                 105                 110

Cys Gln Gln His Tyr Thr Thr Pro Pro Thr Phe Gly Gln Gly Thr Lys
        115                 120                 125

Val Glu Ile Lys Ser Asp Met Pro Met Ala Asp Pro Asn Arg Phe Arg
    130                 135                 140

Gly Lys Asn Leu Val Phe His Ser Glu Val Gln Leu Val Glu Ser Gly
145                 150                 155                 160

Gly Gly Leu Val Gln Pro Gly Gly Ser Leu Arg Leu Ser Cys Ala Ala
                165                 170                 175

Ser Gly Phe Asn Ile Lys Asp Thr Tyr Ile His Trp Val Arg Gln Ala
            180                 185                 190
```

```
Pro Gly Lys Gly Leu Glu Trp Val Ala Arg Ile Tyr Pro Thr Asn Gly
            195                 200                 205

Tyr Thr Arg Tyr Ala Asp Ser Val Lys Gly Arg Phe Thr Ile Ser Ala
    210                 215                 220

Asp Thr Ser Lys Asn Thr Ala Tyr Leu Gln Met Asn Ser Leu Arg Ala
225                 230                 235                 240

Glu Asp Thr Ala Val Tyr Tyr Cys Ser Arg Trp Gly Asp Gly Phe
                245                 250                 255

Tyr Ala Met Asp Tyr Trp Gly Gln Gly Thr Leu Val Thr Val Ser Ser
            260                 265                 270

Ser Gly Gly Gly Ser Gly Ser Gly Leu Asp Gln Leu Thr Asp Pro Pro
            275                 280                 285

Gly Val Arg Arg Val Tyr His Ile Gln Ala Gly Leu Pro Asp Pro Phe
    290                 295                 300

Gln Pro Pro Ser Leu Pro Ile Thr Val Tyr Tyr Ala Val Leu Glu Arg
305                 310                 315                 320

Ala Cys Arg Ser Val Leu Leu Asn Ala Pro Ser Glu Ala Pro Gln Ile
                325                 330                 335

Val Arg Gly Ala Ser Glu Asp Val Arg Lys Gln Pro Tyr Asn Leu Thr
            340                 345                 350

Ile Ala Trp Phe Arg Met Gly Gly Asn Cys Ala Ile Pro Ile Thr Val
            355                 360                 365

Met Glu Tyr Thr Glu Cys Ser Tyr Asn Lys Ser Leu Gly Ala Cys Pro
    370                 375                 380

Ile Arg Thr Gln Pro Arg Trp Asn Tyr Tyr Asp Ser Phe Ser Ala Val
385                 390                 395                 400

Ser Glu Asp Asn Leu Gly Phe Leu Met His Ala Pro Ala Phe Glu Thr
                405                 410                 415

Ala Gly Thr Tyr Leu Arg Leu Val Lys Ile Asn Asp Trp Thr Glu Ile
            420                 425                 430

Thr Gln Phe Ile Leu Glu His Arg Ala Lys Gly Ser Cys Lys Tyr Ala
            435                 440                 445

Leu Pro Leu Arg Ile Pro Pro Ser Ala Cys Leu Ser Pro Gln Ala Tyr
    450                 455                 460

Gln Gln Gly Val Thr Val Asp Ser Ile Gly Met Leu Pro Arg Phe Ile
465                 470                 475                 480

Pro Glu Asn Gln Arg Thr Val Ala Val Tyr Ser Leu Lys Ile Ala Gly
                485                 490                 495

Trp His Gly Pro Lys Ala Pro Tyr Thr Ser Thr Leu Leu Pro Pro Glu
            500                 505                 510

Leu Ser Glu Thr Pro Asn Ala Thr Gln Pro Glu Leu Ala Pro Glu Asp
            515                 520                 525

Pro Glu Asp Ser Ala Leu Leu Glu Asp Pro Val Gly Thr Val Ala Pro
530                 535                 540

Gln Ile Pro Pro Asn Trp His Ile Pro Ser Ile Gln Asp Ala Ala Thr
545                 550                 555                 560

Pro Tyr His Pro Pro Ala Thr Pro Asn Asn Met Gly Leu Ile Ala Gly
                565                 570                 575

Ala Val Gly Gly Ser Leu Leu Ala Ala Leu Val Ile Cys Gly Ile Val
            580                 585                 590

Tyr Trp Met Arg Arg Arg Thr Gln Lys Ala Pro Lys Arg Ile Arg Leu
            595                 600                 605

Pro His Ile Arg Glu Asp Asp Gln Pro Ser Ser His Gln Pro Leu Phe
```

Tyr
625

<210> SEQ ID NO 43
<211> LENGTH: 1953
<212> TYPE: DNA
<213> ORGANISM: Artificial
<220> FEATURE:
<223> OTHER INFORMATION: HSV gD and single chain antibody

<400> SEQUENCE: 43

```
atggggggggg ctgccgccag gttgggggcc gtgattttgt ttgtcgtcat agtgggcctc      60
catggggtcc gcggcaaata tgccttggcg gatgcctctc tcaagatggc cgaccccaat     120
cgctttcgcg gcaaaggaat tccggtctcc gatatccaga tgacccagtc cccgagctcc     180
ctgtccgcct ctgtgggcga tagggtcacc atcacctgcc gtgccagtca ggatgtgaat     240
actgctgtag cctggtatca acagaaacca ggaaaagctc gaagcttct gatttactcg      300
gcatccttcc tctactctgg agtcccttct cgcttctctg tagccgttc cgggacggat      360
ttcactctga ccatcagcag tctgcagccg aagacttcg caacttatta ctgtcagcaa      420
cattatacta ctcctcccac gttcggacag ggtaccaagg tggagatcaa atcggatatg     480
ccgatgctg atccgaaccg tttccgcggt aagaacctgg ttttcattc tgaggttcag       540
ctggtggagt ctggcggtgg cctggtgcag ccagggggct cactccgttt gtcctgtgca     600
gcttctggct tcaacattaa agacacctat atacactggg tgcgtcaggc cccgggtaag     660
ggcctggaat gggttgcaag gatttatcct acgaatggtt atactagata tgccgatagc     720
gtcaagggcc gttcactat aagcgcagac acatccaaaa acacagccta cctacaaatg      780
aacagcttaa gagctgagga cactgccgtc tattattgta gccgctgggg aggggacggc     840
ttctatgcta tggactactg gggtcaagga acactagtca ccgtctcctc gagtggcggt     900
ggctctggtt ccggtctgga ccagctgacg gatcctccgg gggtccggcg cgtgtaccac     960
atccaggcgg gcctaccaga cccgttccag cccccagcc tcccgatcac ggtttactac    1020
gccgtgttgg agcgcgcctg ccgcagcgtg ctcctaaacg caccgtcgga ggccccccag    1080
attgtccgcg gggcctccga agacgtccgg aaacaaccct acaacctgac catcgcttgg    1140
tttcggatgg aggcaactg tgctatcccc atcacggtca tggagtacac cgaatgctcc    1200
tacaacaagt ctctgggggc ctgtcccatc cgaacgcagc cccgctggaa ctactatgac    1260
agcttcagcg ccgtcagcga ggataacctg ggttcctga tgcacgcccc cgcgtttgag    1320
accgccggca cgtacctgcg gctcgtgaag ataaacgact ggacggagat tacacagttt    1380
atcctggagc accgagccaa gggctcctgt aagtacgccc tccgctgcg catccccccg     1440
tcagcctgcc tgtccccca ggcctaccag caggggtga cggtggacag catcgggatg      1500
ctgccccgct tcatcccga gaaccagcgc accgtcgccg tatacagctt gaagatcgcc    1560
gggtggcacg ggcccaaggc ccatacacg agcaccctgc tgcccccgga gctgtccgag    1620
accccccaacg ccacgcagcc agaactcgcc ccggaagacc ccgaggattc ggccctcttg    1680
gaggaccccg tggggacggt ggcgccgcaa atcccaccaa actggcacat accgtcgatc    1740
caggacgccg cgacgccttta ccatccccccg gccaccccga caacatgggg cctgatcgcc    1800
ggcgcggtgg cgcagtct cctggcagcc ctggtcattt gcggaattgt gtactggatg    1860
cgccgccgca ctcaaaaagc cccaaagcgc atacgcctcc ccacatccg ggaagacgac    1920
```

```
cagccgtcct cgcaccagcc cttgttttac tag                                  1953
```

<210> SEQ ID NO 44
<211> LENGTH: 8
<212> TYPE: PRT
<213> ORGANISM: herpes simplex virus

<400> SEQUENCE: 44

Lys Tyr Ala Leu Ala Asp Ala Ser
1               5

<210> SEQ ID NO 45
<211> LENGTH: 18
<212> TYPE: PRT
<213> ORGANISM: herpes simplex virus

<400> SEQUENCE: 45

Tyr His Ile Gln Ala Gly Leu Pro Asp Pro Phe Gln Pro Pro Ser Leu
1               5                   10                  15

Pro Ile

<210> SEQ ID NO 46
<211> LENGTH: 22
<212> TYPE: PRT
<213> ORGANISM: herpes simplex virus

<400> SEQUENCE: 46

Ile Gln Ala Gly Leu Pro Asp Pro Phe Gln Pro Pro Ser Leu Pro Ile
1               5                   10                  15

Thr Val Tyr Tyr Ala Val
            20

<210> SEQ ID NO 47
<211> LENGTH: 9
<212> TYPE: PRT
<213> ORGANISM: herpes simplex virus

<400> SEQUENCE: 47

Gln Gly Val Thr Val Asp Ser Ile Gly
1               5